(12) United States Patent
Joseph et al.

(10) Patent No.: US 9,320,832 B2
(45) Date of Patent: Apr. 26, 2016

(54) ELECTROCHEMICAL DISINFECTION OF IMPLANTED CATHETERS

(75) Inventors: Jose P. Joseph, Palo Alto, CA (US); Pablo E. Garcia, Menlo Park, CA (US); Karen F. Shakespear, San Francisco, CA (US); Sarah Young, Menlo Park, CA (US); Janus A. J. Haagensen, Menlo Park, CA (US); Sanjeev Dutta, Los Altos, CA (US)

(73) Assignees: SRI INTERNATIONAL, Menlo Park, CA (US); The Board of Trustees of the Leland Stanford Junior University, Palo Alto, CA (US)

( * ) Notice: Subject to any disclaimer, the term of this patent is extended or adjusted under 35 U.S.C. 154(b) by 848 days.

(21) Appl. No.: 13/528,788

(22) Filed: Jun. 20, 2012

(65) Prior Publication Data

US 2013/0041238 A1     Feb. 14, 2013

Related U.S. Application Data

(60) Provisional application No. 61/499,066, filed on Jun. 20, 2011, provisional application No. 61/499,529, filed on Jun. 21, 2011.

(51) Int. Cl.
*A61M 25/00* (2006.01)
*A61L 29/04* (2006.01)
(Continued)

(52) U.S. Cl.
CPC .............. *A61L 29/04* (2013.01); *A61L 29/14* (2013.01); *A61M 25/0017* (2013.01); *A61N 1/205* (2013.01); *A61L 2/03* (2013.01);
(Continued)

(58) Field of Classification Search
CPC .............................. A61M 25/0017; A61L 2/03
USPC ....................................................... 422/28, 29
See application file for complete search history.

(56) References Cited

U.S. PATENT DOCUMENTS

| 5,312,813 A | 5/1994 | Costerton et al. |
|---|---|---|
| 5,328,451 A | 7/1994 | Davis et al. |

(Continued)

FOREIGN PATENT DOCUMENTS

| EP | 1291033 | 3/2003 |
|---|---|---|
| EP | 2161040 | 3/2010 |
| WO | WO 98/31420 | 7/1998 |

OTHER PUBLICATIONS

K'Owino et al. Impedance Spectroscopy: A Powerful Tool for Rapid Biomolecular Screening and Cell Culture Monitoring. Electroanalysis 17, 2005, No. 23, 2101-2113.*

(Continued)

*Primary Examiner* — Sean E Conley
*Assistant Examiner* — Donald Spamer
(74) *Attorney, Agent, or Firm* — Richard Aron Osman

(57) ABSTRACT

An implantable catheter is provided that may be disinfected without removal from the body of a patient, using an electrochemical method to generate an electric field on the catheter surface and thus destroy microorganisms in a biofilm that is present or forming. A catheter system includes the implantable catheter and a voltage source that is operably connected to electrodes on or embedded in the exterior and optionally the interior catheter surface. Methods are also provided for disinfecting the implantable catheter in vivo and for detecting or confirming the presence of a pathogenic biofilm thereon.

48 Claims, 15 Drawing Sheets
(11 of 15 Drawing Sheet(s) Filed in Color)

(51) Int. Cl.
*A61L 29/14* (2006.01)
*A61N 1/20* (2006.01)
*A61L 2/03* (2006.01)

(52) U.S. Cl.
CPC ......... *A61L 2202/11* (2013.01); *A61L 2202/24* (2013.01); *A61L 2400/18* (2013.01); *A61M 2025/0019* (2013.01); *A61M 2025/0056* (2013.01)

(56) References Cited

U.S. PATENT DOCUMENTS

| | | | |
|---|---|---|---|
| 5,409,467 | A | 4/1995 | Raad |
| 5,462,644 | A | 10/1995 | Woodson |
| 5,695,482 | A | 12/1997 | Kaldany |
| 5,779,912 | A | 7/1998 | Gonzalez-Martin et al. |
| 5,879,342 | A | 3/1999 | Kelley |
| 6,004,438 | A | 12/1999 | Woodson |
| 6,027,476 | A | 2/2000 | Sterman |
| 6,258,249 | B1 | 7/2001 | Simpson |
| 6,366,807 | B1 | 4/2002 | Kosiba et al. |
| 7,621,929 | B2 | 11/2009 | Nita |
| 7,744,555 | B2 | 6/2010 | DiMauro et al. |
| 8,233,957 | B2 | 7/2012 | Merz et al. |
| 8,267,883 | B2 | 9/2012 | DiMauro et al. |
| 2003/0125679 | A1 | 7/2003 | Kubota et al. |
| 2003/0132144 | A1* | 7/2003 | Herbert-Guillou et al. .... 210/86 |
| 2005/0175658 | A1 | 8/2005 | Demauro et al. |
| 2006/0004317 | A1 | 1/2006 | Mauge et al. |
| 2006/0208384 | A1* | 9/2006 | Mnatsakanyan et al. ..... 264/105 |
| 2007/0279839 | A1 | 12/2007 | Miller |
| 2008/0140052 | A1 | 6/2008 | Moller |
| 2010/0010327 | A1 | 1/2010 | Merz |
| 2010/0087788 | A1 | 4/2010 | Rosenblatt |
| 2010/0233021 | A1 | 9/2010 | Sliwa |
| 2010/0256607 | A1 | 10/2010 | Burnett |
| 2010/0317948 | A1 | 12/2010 | DiMauro |
| 2011/0053144 | A1 | 3/2011 | Garcia Aljaro et al. |

OTHER PUBLICATIONS

"Current Density" Wikipedia. Archieved version from Jun. 16, 2010.*

Del Pozo (Jan. 2009), "The Electricidal Effect: Reduction of *Staphylococcus* and Pseudomonas Biofilms by Prolonged Exposure to Low-Intensity Electrical Current," Antimicrobial Agents and Chemotherapy, pp. 41-45.

Donlan (Mar. 1, 2001), "Biofilms and Device Associated Infections," Emerging Infectious Diseases 7(2).

Dunlop et al., "Detection and Removal of Pathogenic Biofilms on Medical Implant Surfaces," Personalised Health Management Systems, C.D. Nugent et al., Eds.

Elliott (2000), "Intravascular Catheter-Related Sepsis—Novel Methods of Prevention," Intensive Care Med. 26:S45-S50.

Ganesh et al. (2008), "Fiber-Optic Sensors for the Estimation of Oxygen Gradients within Biofilms on Metals," Optics and Lasers in Engineering 46:3217-327.

Liu et al. (1993), "The Effects of Electric Current on Bacteria Colonising Intravenous Catheters," Journal of Infection 27:261-269.

Ohko et al. (2001) "Self-Sterilizing and Self-Cleaning of Silicone Catheters Coated with TiO2 Photocatalyst Thin Films: A Preclinical Work," J. Biomed. Mater. Res. 58:97-101.

Oliver et al. (2006), "An Impedimetric Sensor for Monitoring the Growth of *Staphylococcus* Epidermis," Proc. 28th IEEE EMBS Annual Int'l Conf, Aug. 30-Sep. 8, 2006.

Ryder (Aug. 18, 2005), "Catheter-Related Infections: It's All About Biofilm," Topics in Advanced Practice Nursing eJournal 5(3).

Sekiguchi et al. (2007), "Self-Sterilizing Catheters with Titanium Dioxide Photocatalyst Thin Films for Clean Intermittent Catheterization: Basis and Study of Clinical Use," Int. J. Urology 14:426-430.

Yao et al. (2007), "Self-Sterilization Using Silicone Catheters Coated With Ag and TiO2 Nanocomposite Thin Film," J. Biomed. Mater. Res., Part B: Applied Biomaterials, pp. 453-460.

Liu et al. Mechanisms of the bactericidal activity of low amperage electric current (DC),J Antimicrobial Chemotherapy (1997) 39, 687-695.

International Search Report and Written Opinion in PCT/US2012/043403.

International Search Report and Written Opinion in PCT/US2012/043409.

* cited by examiner

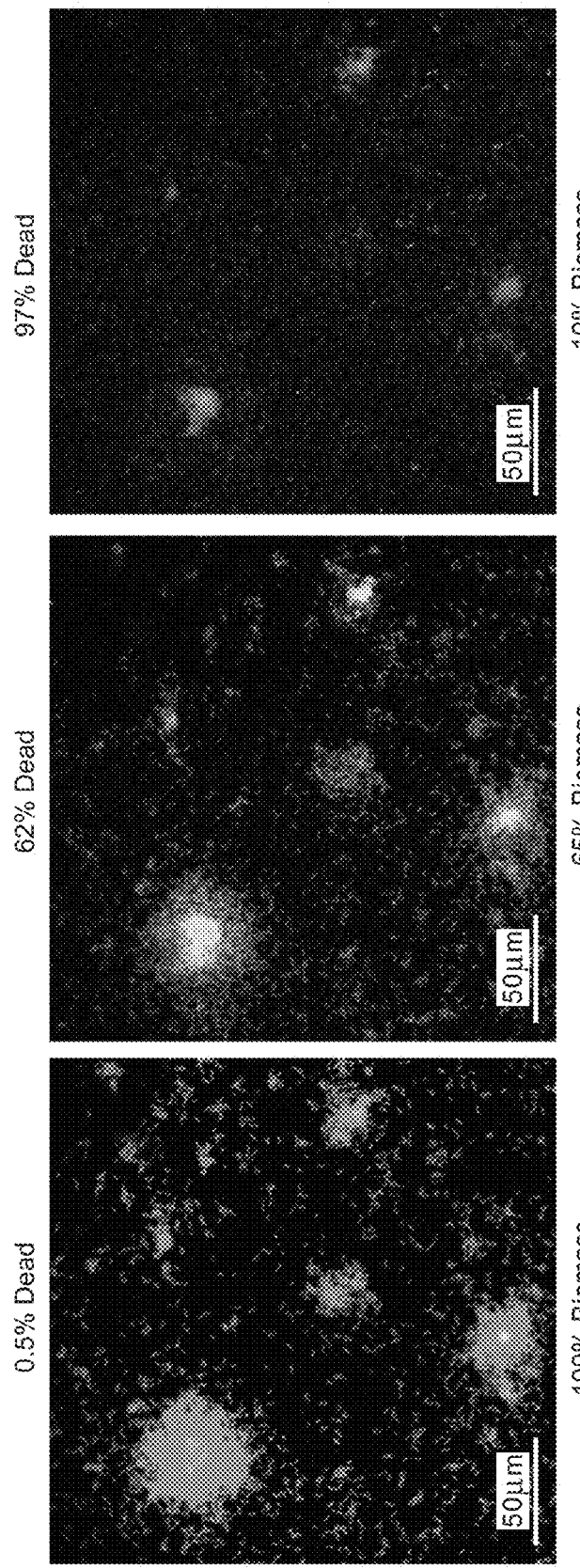

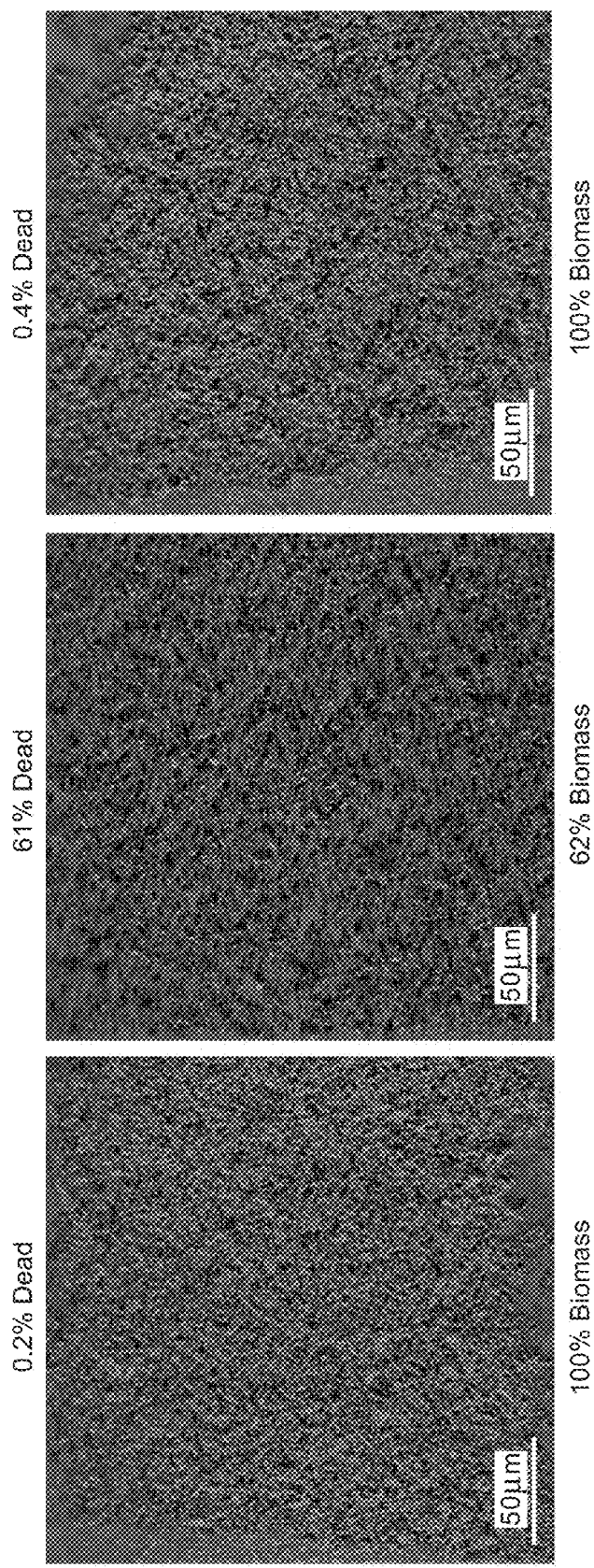

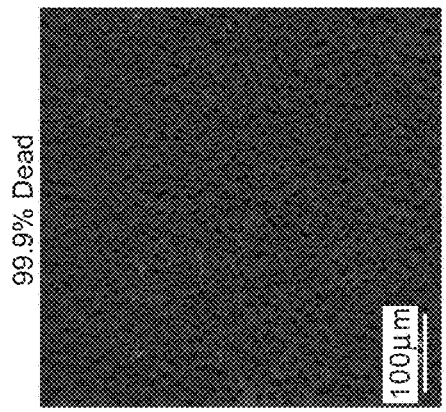
FIG. 10C 99.9% Dead
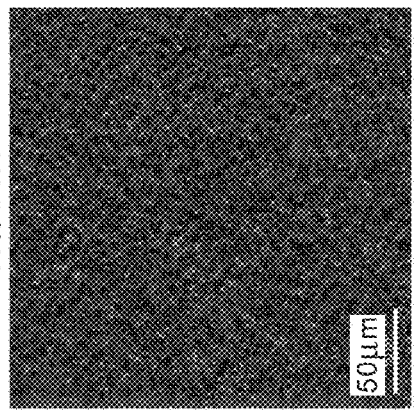
FIG. 10E 90% Dead — Cathode/Anode Switch
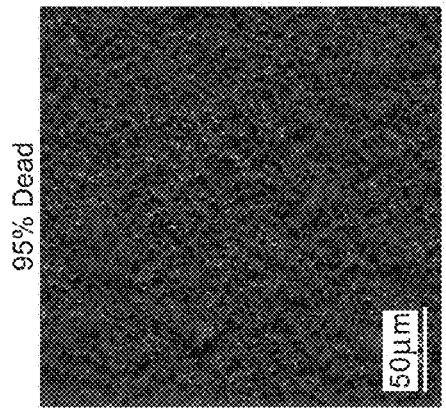
FIG. 10B 95% Dead
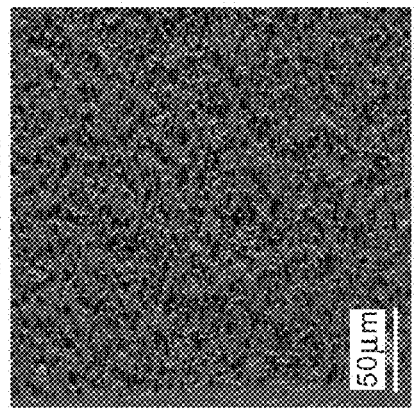
FIG. 10D 2.7% Dead — Cathode/Anode Switch
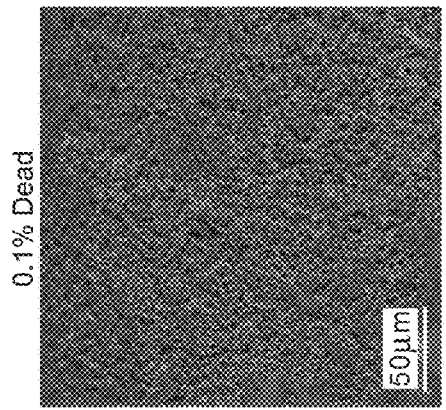
FIG. 10A 0.1% Dead

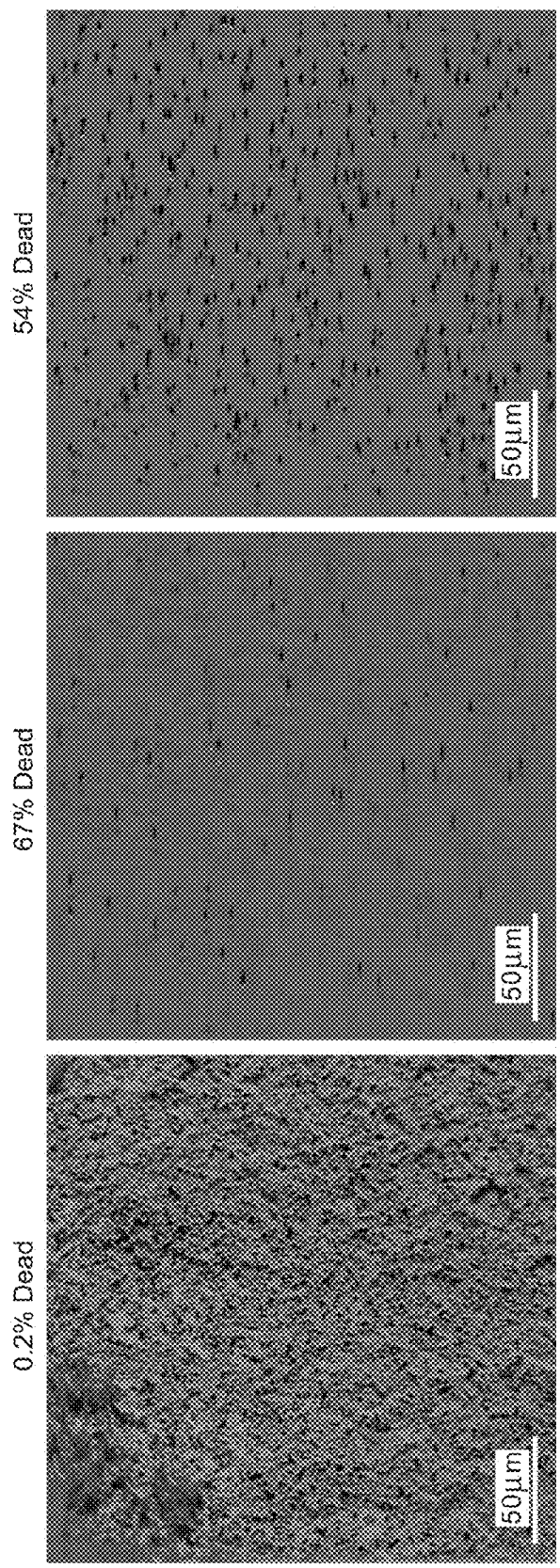

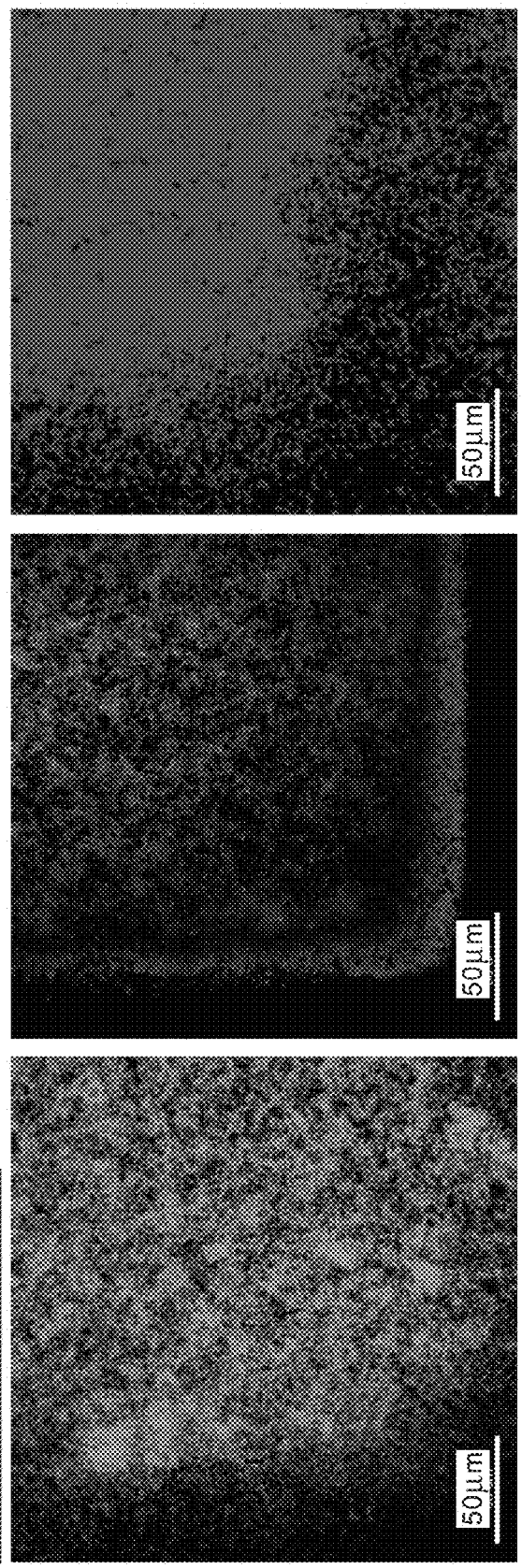
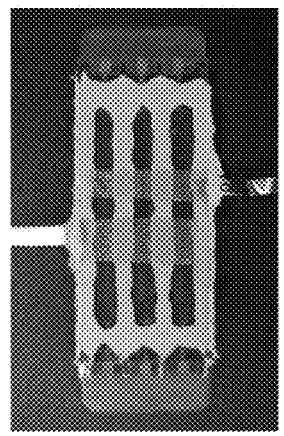
*FIG. 12A*
*FIG. 12B*
*FIG. 12C*

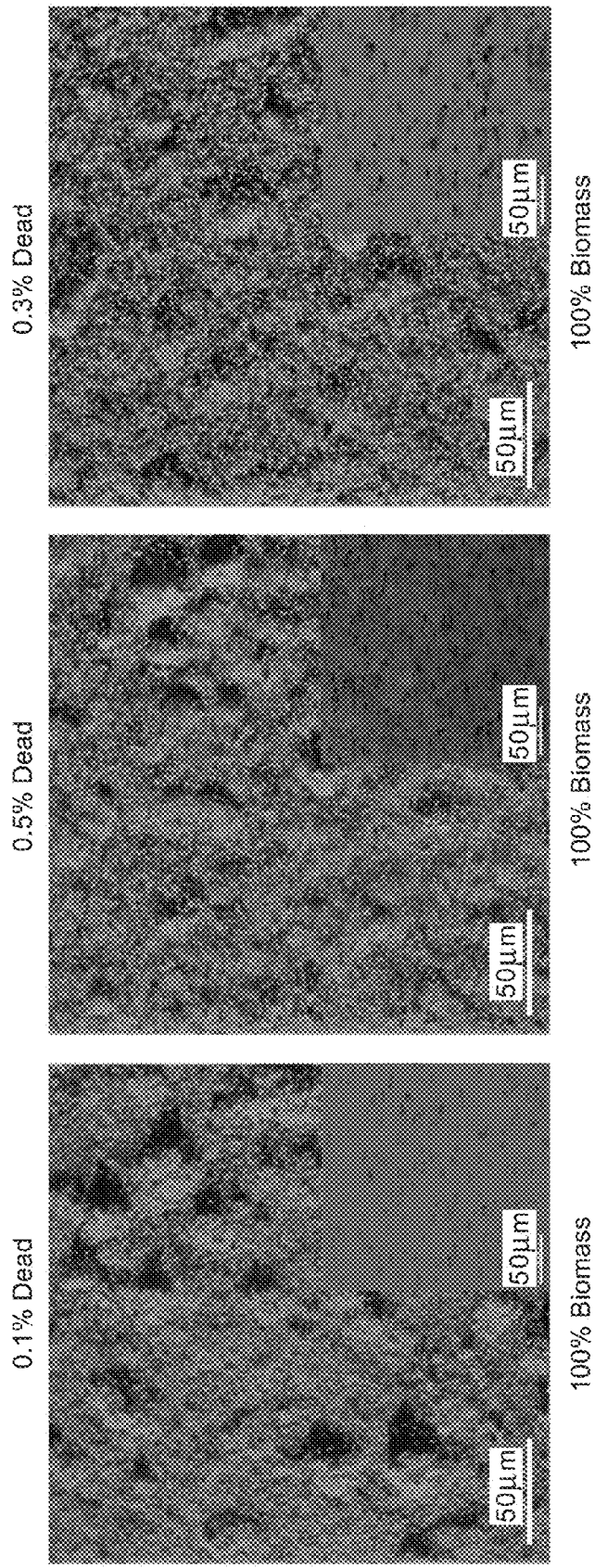

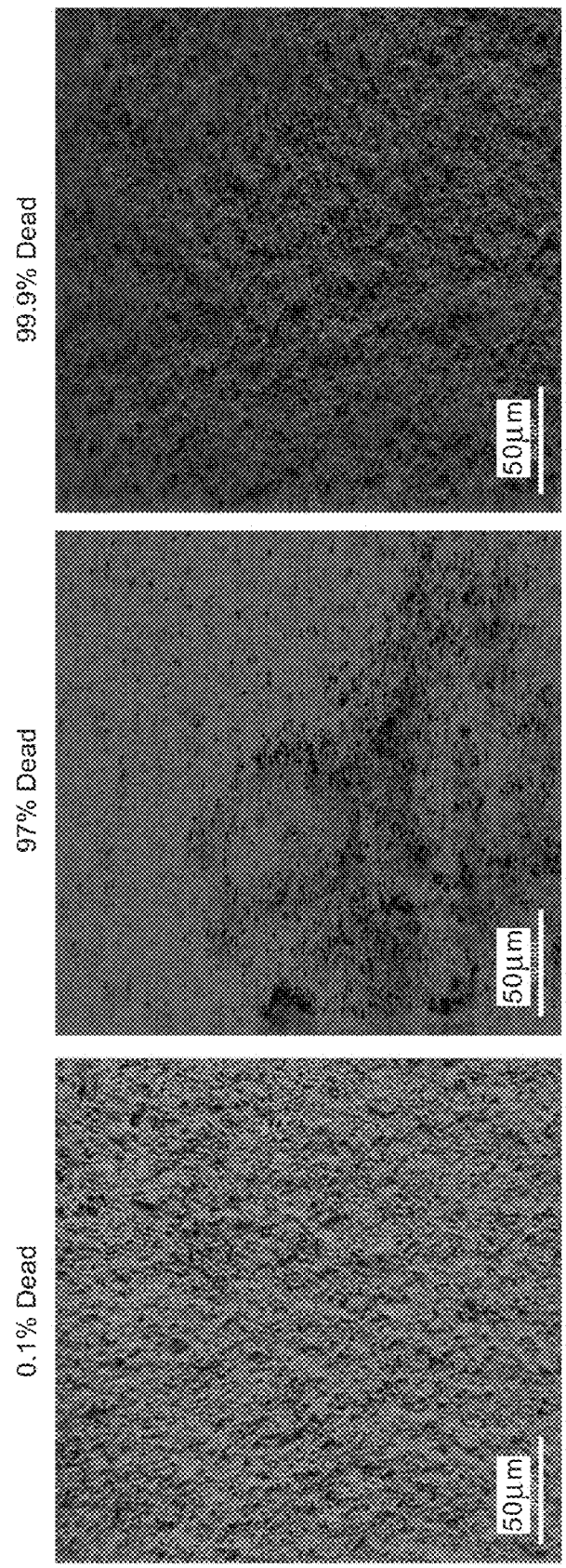

13% Biomass 1.1% Biomass 9.6% Biomass 0.9% Biomass

100% Biomass

100% Biomass

ELECTROCHEMICAL DISINFECTION OF IMPLANTED CATHETERS

CROSS-REFERENCE TO RELATED APPLICATIONS

This application claims priority under 35 U.S.C. §119(e)(1) to provisional U.S. Patent Application Ser. Nos. 61/499,066, filed Jun. 20, 2011, 61/499,529, filed Jun. 21, 2011, and 61/648,484 filed May 17, 2012, the disclosures of all of which are incorporated by reference herein.

This invention was made with Government support under grant number 1P50FD003782-01 awarded by the Food and Drug Administration. The Government has certain rights in this invention.

TECHNICAL FIELD

The invention relates generally to implantable, "indwelling" catheters. More particularly, the invention relates to systems and methods for detecting the presence of a biofilm on a catheter surface and killing microorganisms in the biofilm, without removal of the catheter from a patient's body.

BACKGROUND

Microbial biofilms are formed when microorganisms adhere to a biotic or abiotic surface and produce extracellular macromolecules that facilitate adhesion to the surface and form a structural matrix that supports and protects the microorganisms. A biofilm is thus an accumulation of microorganisms such as bacteria embedded in an extracellular hydrated matrix primarily composed of exopolymers and other filamentous macromolecules, typically glycopeptides. Accordingly, a biofilm is generally described as a layer of bacteria (or other microorganisms), or as a plurality of layers and/or regions on a surface wherein bacteria are encased in a matrix of extracellular polymeric substances, or "EPS." A substantial fraction of the biofilm is actually composed of this matrix; see, e.g., Donlan (2001) *Emerging Infectious Diseases* 7(2): 277-281, Microorganisms in biofilms in many cases exhibit characteristics that are different from those seen with planktonic (freely suspended) microorganisms, particularly with respect to phenotypic traits like growth rate and resistance to antimicrobial treatment. It has been established that bacteria within biofilms can have up to a 1000-fold greater resistance to antibiotic agents than those grown under planktonic conditions, making eradication of a biofilm extremely difficult; see, e.g., Ceri et al. (1999) *J. Clin. Microbiol.* 37(6):1771-1776). One reason for this is the relative impenetrability of the biofilm—which can be both dense and thick—to antimicrobial agents. Another reason can be that the phenotype of sub-populations of cells in the biofilm changes so that the cells can better survive in the presence of antimicrobial agents; see Haagensen et al. (2007) *J. Bacteriol.* 189:28-37, and Folkesson and Haagensen et al. (2008) PLOSone, 3:e1891. Stability and resistance to dissolution are also key features of microbial biofilms; see Saville et al. (2011) *J. Bacteriol.* 193(13): 3257-64. An additional cause of antibiotic resistance may be that upregulation of efflux pumps can render biofilm cells able to transport unwanted antimicrobial agents out of cells in the biofilm; see Costa et al. (Oct. 27, 2011) *BMC Microbiol.* 11:241 and Nikaido et al. (2012) *FEMS Microbiol. Rev.* 36(2):340-63.

While biofilms can and do form on a variety of surfaces in a virtually unlimited number of contexts, biofilm formation in the medical arena is particularly concerning. As noted above, biofilm-related infections are extraordinarily tolerant to treatment with antimicrobial agents, and biofilm formation on medical implants is therefore extremely problematic. Microorganisms can attach to and develop biofilms on any type of medical implant, whether temporarily or permanently inserted or implanted in a patient's body, and can be a source of chronic bacterial infections. Chronic infections that are caused by biofilms on a medical implant (e.g., otitis media and osteomyelitis) often result in treatment failure and reoccurrence shortly after treatment. In 2005, biofilms accounted for about 65% of infections treated in the developed world. See Costerton et al. (1999) *Science* 284:1318-1322.

Medical devices are critical in modern-day medical practice. At the same time, they are major contributors to morbidity and mortality. The use of a medical device, particularly an implanted medical device or medical "implant," is the greatest exogenous predictor of healthcare-associated infection; Manangan et al. (2002) *Emerg. Infect. Dis.* 8:233-236. Most infections that arise in the hospital setting, or "nosocomial" infections, occur primarily at four sites within the body: the urinary tract; the respiratory tract; the bloodstream; and surgical wound sites. According to Ryder et al. (2005) *Topics in Advanced Practice Nursing eJournal* 5(3), the following chronic diseases occurring in the nosocomial context have been established as caused by or at least associated with biofilms: cystic fibrosis; endocarditis; otitis media; prostatitis; osteomyelitis; chronic wounds; myeloidosis; tonsillitis; periodontitis; dental caries; necrotizing fasciitis; biliary tract infection; and Legionnaire's disease.

It has been found that 95% of nosocomial urinary tract infections are caused by an infected urinary catheter, 86% of nosocomial pneumonias are caused by an infected mechanical ventilator, and 87% of nosocomial bloodstream infections are associated with an infected intravascular device. See Ryder et al., supra, citing Richards et al. (1999) *Crit. Care Med.* 27:887-892. As will be explained infra, nosocomial bloodstream infections associated with an implanted catheter are the most life threatening of the aforementioned nosocomial infections and associated with the most significant medical costs.

The medical implants must be removed in order to remove the biofilm and then re-inserted into a patient's body. Examples of implantable medical devices on which biofilms may form include, without limitation:

Catheters, e.g., arterial catheters, central venous catheters, dialysis tubing, endotracheal tubes, enteral feeding tubes, gastrostomy tubes, hemodialysis catheters, nasogastric tubes, nephrostomy tubing, pulmonary artery catheters, tracheostomy tubes, umbilical catheters, and urinary catheters;

Implants, e.g., arteriovenous shunts, breast implants, cardiac and other monitors, cochlear implants, defibrillators, dental implants, maxillofacial implants, middle ear implants, neurostimulators, orthopedic devices, pacemaker and leads, penile implants, prosthetic devices, replacement joints, spinal implants, and voice prostheses; and Other implanted devices such as artificial hearts, contact lenses, fracture fixation devices, infusion pumps, insulin pumps, intracranial pressure devices, intraocular lenses, intrauterine devices, joint prostheses, mechanical heart valves, ommaya reservoirs, suture materials, urinary stents, vascular assist devices, vascular grafts, vascular shunts, and vascular stents.

As indicated above, catheters are of particular interest because they are used in a host of medical applications and often involve critically ill and/or very young patients. Catheters are used not only in the administration of fluids and medication, but also in drainage of body fluids such as urine or abdominal fluids; angioplasty, angiography, and catheter ablation; administration of gases such as oxygen and volatile anesthetic agents; and hemodialysis. A central venous catheter (also referred to as a "central line" or "CVC") is a widely used catheter that is placed in a large vein in the neck, chest, or groin and serves as a conduit for delivering medications, parenteral nutrition, and fluids. A CVC is commonly used in plasmapheresis, dialysis, and chemotherapy, and is also relied upon to obtain critically important measurements, such as central venous pressure ("CVP").

Catheter-associated bloodstream infections (CABSIs; also referred to as catheter-related bloodstream infections, or CRBSIs) are a leading cause of morbidity and mortality in hospital settings. Each year 250,000 documented CABSIs occur in the United States, with an attributable mortality in the range of about 12% to 25% and an estimated cost to treat of $25,000 per episode ($6.2 billion annually, as of 2002). The intensive care environment accounts for 80,000 of these infections, with an attributable mortality as high as 35% and a cost to treat at $56,000 per episode. See Department of Health & Human Services, USA: Guidelines for the Prevention of Intravascular Catheter-Related Infections, 2011. Diagnosis is difficult and clinical suspicion of infection frequently leads to removal and replacement of indwelling catheters, resulting in significant healthcare costs and requiring that patients be subjected to additional procedures. The approaches that have been taken to counteract the widespread problem have not succeeded in either preventing biofilm formation or eliminating a biofilm that has formed without removal of the catheter from a patient's body.

While biofilm formation is generally problematic with implantable medical devices, it will be appreciated that the risk of infection is that much higher with catheters such as the CVC that remain in place for an extended time period. The most common bacteria found in CVC biofilms are *Staphylococcus aureas, Staphylococcus epidermis sepsis, Candida albicans, Pseudomonas aeruginosa, Klebsiella pneumoniae*, and *Enterococcus faecalis*. These bacteria may originate from patient's skin microflora, exogenous microflora from health care personnel, or contaminated infusions, and can migrate from the skin along the exterior surface or internally from the catheter hub or port.

It has been found that biofilm formation on CVCs is universal and that virtually all in-dwelling CVCs are colonized by microorganisms in a biofilm. Biofilms form not only on the outer surface of the catheter, but also on the inner lumen of the catheter, particularly with long-term catheterization; see Raad et al. (1998) *Lancet* 351:893-98.

The most prevalent approach to preventing CABSIs—hand washing and the use of aseptic techniques when handling the catheter—can be unreliable even in the highly controlled setting of a hospital. Other techniques such as ethanol lock therapy, or "ELT," may degrade catheter materials and are not effective with respect to biofilms that are downstream from the inlet point. Catheters have been made with antibacterial coatings, including minocycline, chlorhexidine, and silver (see Aslam (2008), "Effect of Antibacterials on Biofilms," Section of Infectious Diseases, Assoc. *Prof Infect. Control Epidemiol.* 5175:e9-e11), but the antibacterial efficacy of all of these coated catheters, wanes over time due to coating degradation; moreover, the coating method is not effective against nonbacterial organisms such as fungus, the coatings may selectively target only a particular type of bacteria, they can promote antibiotic resistance, and they are significantly more expensive than typical catheters. (Aslam, supra; Donlan, supra).

In the hospital setting, patients with indwelling catheters who have febrile illness and elevated inflammatory markers are suspected of having a CABSI. Blood cultures drawn from peripheral sites in these patients are compared with those drawn from the suspected catheter. If catheter cultures are positive, a line infection is suspected, particularly if peripheral cultures are negative. This method for verifying catheter infection is highly inaccurate, however, having a high false-positive rate because bacteria from other sources can also result in a positive test result. Thus, a catheter may be identified as infected when it actually is not. Currently, there is no highly specific, sensitive method for detecting catheter infection. Once a catheter is suspected of infection, first-line therapy is typically treatment with antibiotics. However, biofilm formation renders such therapy ineffective, as noted earlier, and antimicrobial agents can single out resistant organisms. In many cases, surgical removal of the catheter is necessary, resulting in increased healthcare costs, additional and sometimes unnecessary surgical procedures for patients, and reduction in potential venous access sites in patients who may be line-dependent for nutrition and pharmacotherapy.

The problem of infection is not limited to venous catheters, but also affects other types of catheters and medical devices as indicated above, such as urinary catheters, ventriculoperitoneal shunts, in-dwelling catheter-like prostheses (vascular conduits), dialysis tubing, endotracheal tubes, Foley catheters, and the like. Based on these considerations, a long-felt need is apparent for technology that can safely and effectively destroy a biofilm, i.e., kill microorganisms in the biofilm. Such a system would have widespread application in medicine, resulting in tremendous savings in healthcare costs, reduced morbidity and mortality, and assist in preventing further antibiotic resistance. It would also be optimal to provide a system that could not only kill microorganisms within a biofilm but also prevent biofilm formation and even sense the formation, presence, or growth of a biofilm. Ideally, such a system would be portable and easily controlled by a patient outside of a hospital setting. It would in addition be beneficial to be able to implement a system that meets the aforementioned requirements in the detection of a biofilm that has formed or is in the process of forming.

SUMMARY OF THE INVENTION

Accordingly, it is a primary object of the invention to address the aforementioned need in the art by providing a method and system for inhibiting a biofilm on the surface of an implanted catheter, i.e., killing microorganisms in a biofilm that is present or forming on the catheter surface.

In one aspect of the invention, an implantable catheter is provided that can be electrochemically disinfected in situ, i.e., without removal of the implanted catheter from the body of a patient, by inhibiting a biofilm on the catheter surface. The implantable catheter comprises: an elongate catheter body having a proximal end, a distal end, at least one lumen extending through the catheter body and adapted to transport fluid from the proximal region to the distal region, an outer surface on the exterior of the catheter body, and an inner surface on the interior of the lumen; at least two exterior electrodes on and integral with the outer surface of the catheter, the exterior electrodes being elongate and extending longitudinally along the outer surface of the catheter body from the proximal end to the distal end; optionally, at least two interior electrodes on and integral with the inner surface of the catheter, the interior electrodes being elongate and extending longitudinally along the outer surface of the catheter body from the proximal end to the distal end; and a means for receiving an applied voltage from a voltage source so that an electric field is generated across the at least two exterior electrodes effective to convert endogenous compounds at the catheter surface to biocidal species. In a related aspect of the invention, the optional interior electrodes are also present, and in another related aspect, interior electrodes are provided on the inner surface, and exterior electrodes are not used.

In another aspect of the invention, an implantable catheter system is provided that includes the implantable catheter and a voltage source, where the voltage source may be a direct current source, an alternating current source, and a pulsed voltage source.

In a further aspect, the invention provides a method for inhibiting a biofilm surface of the implantable catheter described above, where biofilm "inhibition" encompasses killing microorganisms in a biofilm present on the surface of the catheter, and will be defined in further detail infra. The method comprises applying a voltage across at least the exterior electrodes of a magnitude that is effective to create a biofilm-inhibiting concentration of oxidizing agents from endogenous compounds present in the body without causing significant damage to cells and tissues that are not associated with the biofilm. Voltage may be applied intermittently at regular intervals or continuously, for a time period of at least 72 hours. In contrast to prior methods proposed for biofilm destruction, it is important to note that in the present method, the voltage is applied and the electric field thus generated in the absence of an added biocidal agent and in a noninvasive manner, without removing the catheter from a patient's body.

In a related aspect of the invention, the aforementioned method further includes the step of detecting or confirming the presence or formation of a biofilm on at least the outer surface of the catheter prior to applying a voltage across at least the external electrodes on the catheter surface. The method can involve impedance measurement across the electrodes using Electrical Impedance Spectroscopy (EIS) or an alternative technique to measure impedance, as statistically significant increases in impedance across the electrodes are indicative of the formation of a biofilm. Other methods, e.g., oxygen determination at the catheter surface, can also be used.

In another aspect, the invention provides a method for preventing formation of a biofilm on an implantable catheter, again without need for an added biocidal agent and without removal of the catheter from the patient's body. The method involves applying a voltage across at least the exterior electrodes of a magnitude that is effective to create a concentration of oxidizing agents from endogenous compounds present in the body that is sufficient to prevent formation of a biofilm on the catheter surface.

Additional aspects, features, and objects of the invention will become more fully apparent when the Detailed Description below is read in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 7A, 7B, and 7C show images obtained using confocal microscopy of a *P. aeruginosa* biofilm grown for 6 h in minimal static media on a graphite electrode (4 cm in length) and exposed to electrochemistry using −1.2 V at 20 µA/cm². FIG. 7A shows the anode before electrochemical treatment, FIG. 7B shows the anode 40 min after electrochemical treatment was initiated, and FIG. 7C shows the anode after 2 h treatment. The images were obtained 4 cm from the electrode connection to the power supply.

FIGS. 8A, 8B, and 8C show images obtained using confocal microscopy of a *P. aeruginosa* biofilm grown for 6 h in minimal static media on a graphite electrode (4 cm in length) and exposed to electrochemistry using −0.6 V at 10 µA/cm². FIG. 8A shows the anode control without electrochemical treatment 6 h after initial attachment of cells, FIG. 8B shows the anode-associated biofilm 6 h after prophylactic treatment was initiated, and FIG. 8C shows the cathode 6 h after prophylactic treatment was initiated. The images were obtained 4 cm from the electrode connection to the power supply.

FIG. 9A shows the anode control without electrochemical treatment and FIG. 9B shows the anode-associated biofilm 1 h after initiation of electrochemical treatment. The images were obtained 4 cm from the electrode connection to the power supply.

FIGS. 10A, 10B, 10C, 10D, and 10E show images obtained using confocal microscopy of a *P. aeruginosa* biofilm grown for 6 h in minimal static media on a graphite electrode (16 cm in length) and exposed to electrochemistry using −1.2 V at 24 µA/cm². FIG. 10A shows the anode control without treatment 6 h after attachment of cells to the electrode, FIG. 10B shows the anode-associated biofilm after 60 min treatment, FIG. 10C shows the anode after 90 min treatment, FIG. 10D shows the cathode after 60 min treatment, and FIG. 10E shows the cathode of FIG. 10D 30 min after reversing polarity and thereby switching the electrode to an anode. The images were obtained 12 cm from the electrode connection to the power supply.

FIGS. 11A, 11B, and 11C show images obtained using confocal microscopy of a *P. aeruginosa* biofilm grown for 6 h in minimal static media on a graphite electrode (4 cm in length) and exposed to electrochemistry using −0.8 V at 24 µA/cm². FIG. 11A shows the anode control without treatment 6 h after attachment of cells to the electrode, FIG. 11B shows the anode-associated biofilm 6 h after prophylactic treatment was initiated, and FIG. 11C shows the cathode 6 h after prophylactic treatment was initiated. The images were obtained 4 cm from the electrode connection to the power supply.

FIGS. 12A, 12B, and 12C show images obtained using confocal microscopy of a *P. aeruginosa* biofilm grown in glucose minimal media for 24 h in flow chambers on a glass surface supported with a gold electrode grid (grid squares are 400×400 µm), and exposed to electrochemistry using −1.2 V at 20 µA/cm$^2$. FIG. 12B shows the anode 10 min after treatment was initiated, and FIG. 12C shows the anode after 1 h treatment.

FIGS. 13A, 13B, and 13C show images obtained using confocal microscopy of a *P. aeruginosa* biofilm grown in glucose minimal media for 72 h in flow chambers on a glass surface supported with a gold electrode grid (grid squares are 400×400 µm), and exposed to electrochemistry using −1.2 V at 20 µA/cm$^2$. FIG. 13B shows the anode 20 min after treatment was initiated, FIG. 13C shows the anode after 1 h treatment.

FIGS. 14A, 14B, and 14C show images obtained using confocal microscopy of a *P. aeruginosa* biofilm grown in glucose minimal media for 72 h in flow chambers on a 20 cm long graphite electrode, and exposed to electrochemistry using 2 µA/cm$^2$. FIG. 14A shows a control sample after 72 h growth, FIG. 14B shows the anode after 72 h treatment, FIG. 14C shows the cathode after 72 h treatment, and the inset images in FIGS. 14A, 14B, and 14C show dead cells in the inspected area.

FIG. 15A shows a control sample after 72 h growth, FIG. 15B shows the anode after 72 h treatment, and FIG. 15C shows the cathode after 72 h treatment.

FIGS. 17A, 17B, and 17C show images obtained using confocal microscopy of an *E. coli* biofilm grown for 6 h in minimal static media on a graphite electrode (4 cm in length) and exposed to electrochemistry using −0.8 V at 25 µA/cm$^2$. FIG. 17A shows the anode control without electrochemical treatment 6 h after initial attachment of cells, FIG. 17B shows the anode-associated biofilm after 1 h treatment, and FIG. 17C shows the cathode biofilm after 1 h treatment. The images were obtained 4 cm from the electrode connection to the power supply.

FIG. 20A: biofilm and *Staphylococcus aurous* [15981]. FIG. 20B: biofilm grown for 6 h in TSB media on a 4 cm long graphite electrode. Cells were isolated from the graphite electrode before (Control) and after treatment (Anode and Cathode with −0.8V (25 µA/cm$^2$)) followed by plating for determination of CFU/ml. The X-axis shows Control, Anode and Cathode, respectively, and the units on the Y-axis are CFU/ml.

DETAILED DESCRIPTION OF THE INVENTION

I. Definitions and Nomenclature

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise. For example, the term "a thermosetting polymer" can refer to a single thermosetting polymer or to two or more thermosetting polymers in combination, and the term "flexible elastomer" can refer to a single such elastomer or to a composite of two or more such elastomers in combination.

The term "implantable catheter" as used herein refers to a catheter that is implanted or inserted in the human body either temporarily or permanently.

The term "inhibition" as applied to the capability of the invention to inhibit biofilm growth refers to the process of killing microorganisms in a biofilm that is present or forming on a surface, and thus includes all of the following: elimination or destruction of a biofilm; disruption of a biofilm; reduction in the thickness of a biofilm; the killing of some or all of the microorganisms within a biofilm; and prevention of biofilm growth.

The term "disinfection" as used herein refers to biofilm inhibition as defined above, typically referring to the killing of microorganisms within a biofilm on a catheter surface.

The term "biofilm" refers to a matrix-enclosed microbial accretion on and anchored to the surface of an implanted medical device.

The term "biofilm formation" is intended to include the formation, growth, and modification of the bacterial or other colonies contained with biofilm structures, as well as the synthesis and maintenance of the polysaccharide matrix of the biofilm structures.

II. The Implantable Catheter

The implantable catheter of the invention is thus one that can be electrochemically activated to kill infecting microorganisms in a biofilm present on its exterior and/or interior surfaces and/or prevent biofilm growth thereon. The infecting microorganisms in the biofilm are typically bacterial cells, but there may also be colonies of yeast, fungi, mold, or other colonizing microorganisms in the biofilm.

Figure 1:
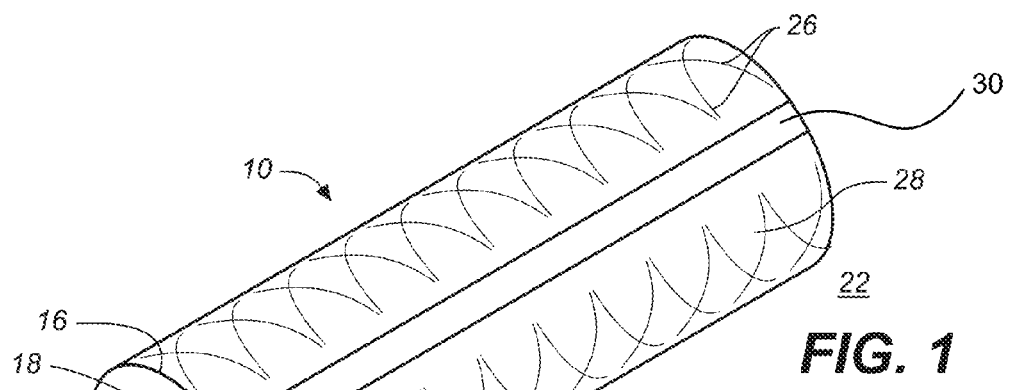
FIG. 1 is a perspective view of a segment of a catheter of the invention with two exterior electrodes.

FIG. 1 illustrates one such catheter, shown generally at 10. As may be seen in the figure, the catheter is composed of an elongate catheter body 12 having a continuous, substantially cylindrical annular wall 14 defining an outer catheter surface 16 and an inner catheter surface 18. The wall 14 of catheter body 12 also defines a central hollow lumen or passageway 20, through which fluid can flow from proximal region 22 to distal region 24 in connection with any of a variety of diverse medical applications. Proximal region 22 terminates in an inflow tip at the proximal end of the catheter, while distal region 24 terminates in an outflow tip at the distal end of the catheter. In general, the outer diameter ("OD"; the distance from outer surface to outer surface across cross-section of the catheter) will be in the range of about 1 mm to 2.5 mm, corresponding to a range of about 3 to 7.5 French ("Fr", where 1 Fr=3×OD in mm). The wall thickness is generally about 0.5 mm, while the catheter length can vary a great deal depending on the application, anywhere from several centimeters to several meters, averaging about 1 m to 2 m in most contexts.

The implantable catheter 10 contains at least two exterior electrodes 26 and 28 integral with the outer surface 16, with one electrode serving as an anode and the other electrode serving as a cathode, as determined by the polarity of the applied voltage. Depending on the method of manufacture, as will be discussed in further detail infra, the electrodes may each be in the form of a very thin film layer on the outer surface, or they may be impressed into the outer surface such that the electrode surface and the catheter surface surrounding the electrode are co-planar. The term "integral" as used herein to specify that the electrodes are "integral with" the outer surface is intended to encompass both alternatives.

Electrodes 26 and 28, as seen in the figure, extend longitudinally along the outer surface from the proximal region to the distal region. The electrodes can be composed of a metallic or nonmetallic element, composition, alloy, or composite that is inert in vivo, including, by way of example: a metal per se, such as gold, platinum, silver, palladium, or the like; an alloy of two or more metals, e.g., a platinum-iridium alloy; a metal-coated substrate, such as a platinum-plated titanium or titanium dioxide substrate, or a platinum- and/or ruthenium-coated nickel substrate; a metal oxide, e.g., ruthenium oxide (i.e., ruthenium (IV) oxide, or $RuO_2$), rhenium oxide (generally rhenium (IV) oxide [$ReO_2$] or a composition of mixed-valence rhenium oxides), iridium oxide, or the like; a metal carbide such as tungsten carbide, silicon carbide, boron carbide, or titanium carbide; graphite; carbon-polymer composite materials, and combinations or mixtures of any of the foregoing.

Electrodes of graphite, carbon-polymer composites, and noble metals are generally preferred.

Noble metal electrodes include, for example, electrodes fabricated from gold, palladium, platinum, silver, iridium, platinum-iridium alloys, platinum-plated titanium, osmium, rhodium, ruthenium, and oxides and carbides thereof.

Carbon-polymer composite electrodes are fabricated from pastes of particulate carbon, e.g., carbon powder, carbon nanoparticles, carbon fibers, or the like, and a thermosetting polymer. Carbon-polymer composite electrodes are particularly desirable, for economic as well as practical reasons. Aside from the relatively low cost of such electrodes, use of a precursor composed of a paste of particulate carbon and a thermosetting or thermoplastic polymer or prepolymer thereof enables manufacture of the implantable catheter via extrusion, with the electrodes extruded along with the polymeric catheter body. Illustrative polymers for this purpose include, without limitation, polyurethanes, polyvinyl chloride, silicones, poly(styrene-butadiene-styrene), polyether- amide block copolymers, and the like. Carbon-polymer pastes for this purpose are readily available commercially, e.g., from ECM, LLC, in Delaware, Ohio. Preferred polymers are thermoplastic. Depending on the polymer system selected for electrode preparation, a polymerization initiator and cross-linking agent may be included in the fabrication mixture.

Electrochemical activation is carried out by creating an electric field across the area of the outer surface 12 so as to generate species that kill microorganisms in any biofilm present or forming on the outer surface. These species, or "biocides," are created upon application of the aforementioned electric field from endogenous compounds present in the body, in the region of the outer surface. The electric field is generated by application of a voltage across electrodes 26 and 28 using a voltage source, which may be a direct current (DC) source, such as a battery, e.g., in the form of a conventional battery back or as part of a miniaturized system that can be placed under a patient's skin (in which the device may be powered wirelessly from a control unit outside the patient's body), or a conventional alternating current (AC) or pulsed voltage source. The catheter thus includes a means for receiving voltage from the voltage source to generate the electric field, e.g., conductive wires in electrical communication with the voltage source and the electrodes. Aside from the fact that the voltage source, e.g., a battery, may render the device portable and usable by the patient, the particular type of device used to generate the electric field is not critical to the practice of the invention, and a wide variety of devices that are capable of generating an electric field of appropriate voltage and amperage may be used. Representative such devices are described in U.S. Pat. Nos. 5,312,813 and 5,462,644.

It is to be appreciated that in operation the applied voltage must be sufficient to generate current flow from electrode to electrode, across the gap 30 that separates the electrodes, which comprises the dielectric material of the catheter body. In general, the gap between the electrodes will be in the range of about 1000 Å to about 2 μm for plated metallic electrodes, and in the range of about 10 μm to about 200 μm for extruded composite electrodes. As alluded to above, an important advantage of the invention is that the biocidal agents, i.e., the chemical species that kill microorganisms in the biofilm present or forming on a surface of the catheter and prevent biofilm growth thereon, are created from materials endogenous to the cells and tissue of the human body in the vicinity of the catheter surface. That is, application of a voltage across the electrodes results in the oxidation of chloride ions at the anode (chloride ions are ubiquitous within the body in the form of dissolved chloride salts), and in the reduction of oxygen at the cathode. The resulting species include the oxidizing agents hydrogen peroxide, superoxide ion, hypochlorous acid, and hypochlorite ion. The biocidal potential of these species is well documented, e.g., in the electrochemical sterilization of salt water.

The material used to form the body 12 of the implantable catheter 10 is necessarily nonconductive, biocompatible, and inert under the conditions of use, with respect to, for example, body fluids and tissue, the reactive biocidal species, and the applied voltage. In addition, the material should also provide the catheter with sufficient flexibility to allow the catheter body 12 to bend, twist, and undergo some degree of deformation. Accordingly, the catheter body 12 is preferably made of a strong yet flexible polymeric material, such as silicone, polyurethane, polyvinyl chloride (PVC), polyamide, polyethylene, polybutylene terephthalate, polyetherimide, polyethylene, polyethylene terephthalate, polyethylene naphthalate, or any combinations thereof. A flexible silicone elastomer is particularly preferred as the material for the catheter body.

Figure 2:
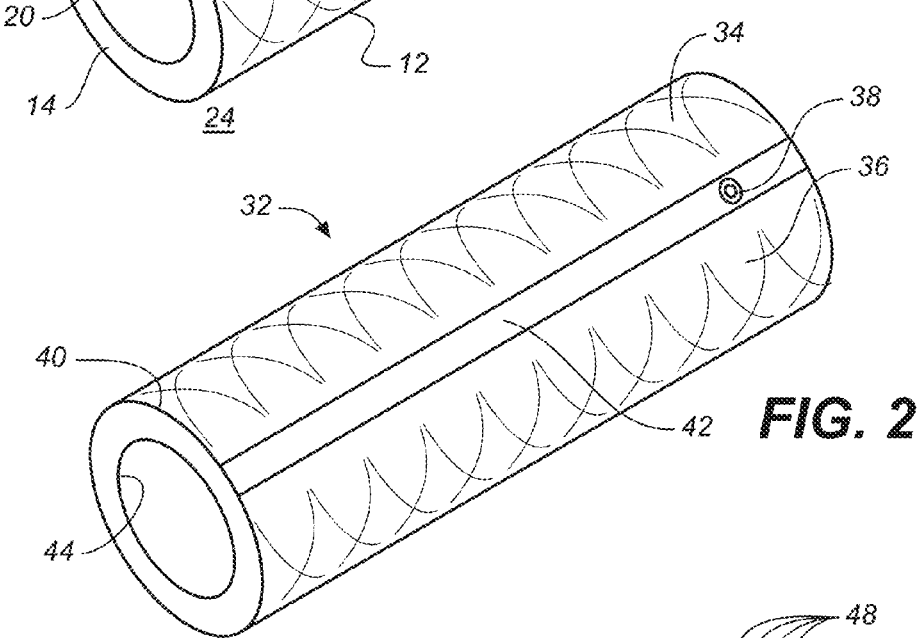
FIG. 2 is a perspective view of a segment of a catheter of the invention with two exterior electrodes and a third point electrode.

In another embodiment, as illustrated in FIG. 2, the implantable catheter shown generally at 32 is provided with two thin film exterior electrodes 34 and 36 and a third electrode that may be a point electrode 38 present on the catheter surface 40 within gap 42, as illustrated. In this embodiment, the third electrode serves as a reference electrode, while electrodes 34 and 36 serve as the working electrode and counter electrode. When the polarity of the applied voltage is reversed, electrodes 34 and 36 will alternate functions. It will be appreciated that the third electrode is not necessarily a point electrode or present on the surface of the catheter. The reference electrode can be a third elongate electrode on the outer surface 16, or it may be located on the inner surface 44 of the catheter or anywhere in a solution that is in contact with the other two electrodes. For instance, the reference electrode can be a simple wire electrode, e.g., a silver wire electrode, placed in the perfusion fluid, in the catheter hub. In this embodiment, a potentiostat can be employed to maintain the potential of the working electrode versus the reference electrode by adjusting the current at the counter electrode, as is known in the art. A voltage source as described with respect to the two-electrode embodiment of FIG. 1 can also be used.

Figure 3:
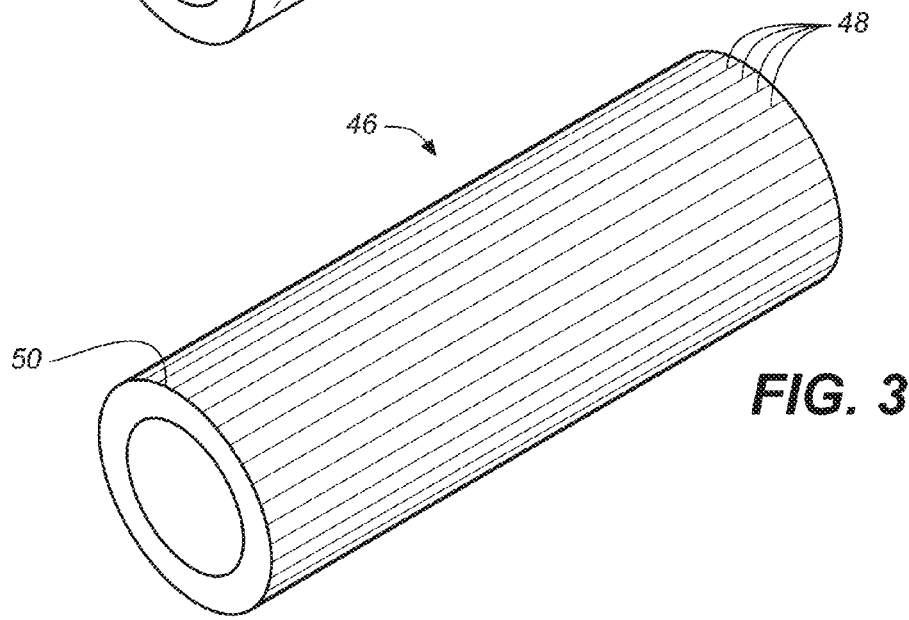
FIG. 3 is a perspective view of a segment of a catheter of the invention with a plurality of exterior electrodes embedded in the outer surface in interdigitated fashion.

In another embodiment, as illustrated in FIG. 3, the implantable catheter shown generally at 46 is provided with a plurality of interdigitated electrodes 48 on outer surface 50. The interdigitated electrodes may be metallic or they may be composed of any of the electrode materials enumerated as candidates for the embodiment of FIG. 1. This configuration can increase the efficiency of the system and may in some cases represent the preferred embodiment. In a related embodiment, two or more flexible mesh electrodes can be used as well, e.g., fabricated from silver or other metallic nanowire, or woven from metal wire and polymer fibers. They may be pressed into the outer surface of the catheter during device manufactured or otherwise incorporated in or attached to the catheter's outer surface. Voltage sources as described for the embodiment of FIG. 1 may be employed here as well.

Figure 4:
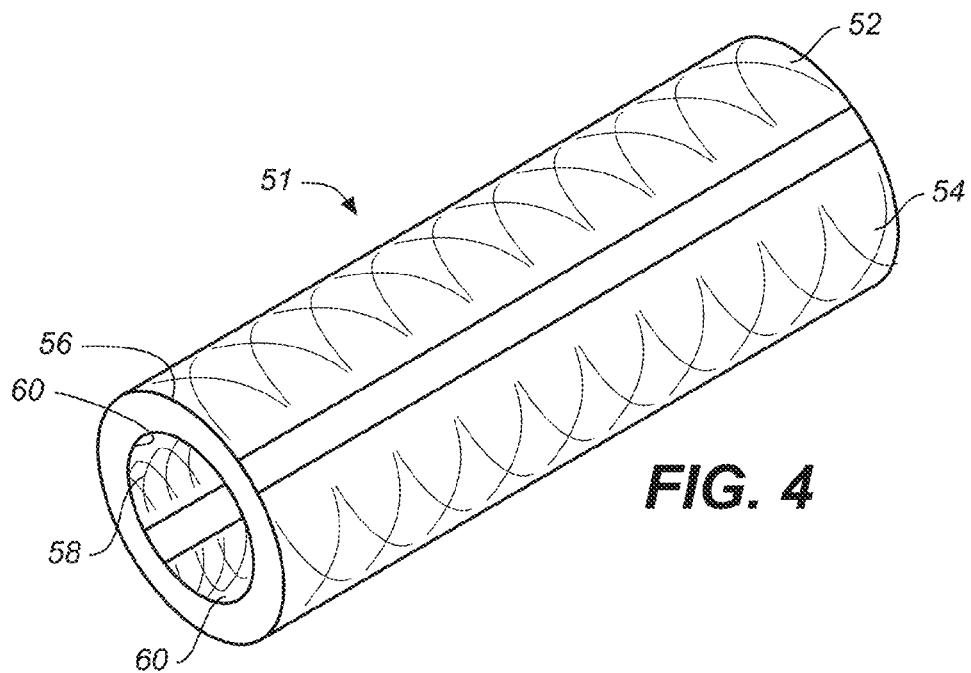
FIG. 4 is a perspective view of a segment of a catheter of the invention with two exterior electrodes embedded in the outer surface and two interior electrodes embedded in the inner surface.

In a further embodiment, as illustrated in FIG. 4, an implantable catheter 48 of the invention is provided with two thin film exterior electrodes 52 and 54 on the outer catheter surface 56 and two additional thin film interior electrodes 58 and 60 on the inner catheter surface 62. In this embodiment, the advantage added by employing interior electrodes is the capability of killing microorganisms within a biofilm present or forming on the inner surface of the catheter as well as on the outer surface. In addition, use of the interior electrodes reduces the likelihood of occlusions that may occur as a result of biofilm buildup on the inner catheter surface. This system may include an additional electrode (not shown) to serve as a reference electrode for both the interior and exterior electrodes, as described above with respect to the embodiment of FIG. 2, or may include two additional electrodes, one serving as a reference electrode for the interior electrodes, and the other serving as a reference electrode for the exterior electrodes.

Figure 5:
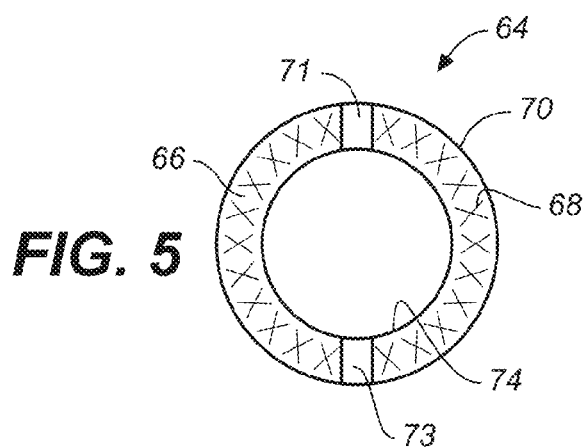
FIG. 5 is a cross-sectional view of an implantable catheter of the invention wherein two electrodes extend from the outer catheter surface through the catheter wall to the inner catheter surface.

In another embodiment, as illustrated in the cross-sectional view of FIG. 5, an implantable catheter 64 according to the invention is provided with two electrodes 66 and 68, each of which extends from the outer catheter surface 70 through the catheter wall 72 to the inner catheter surface 74, and separated by gaps 71 and 73, thus serving as and providing the benefit of a system having interior and exterior electrodes but using a simpler and more economically advantageous design. Because the electrodes extend through the catheter body all the way to the distal terminus of the catheter, this embodiment is advantageous in providing an active catheter tip, ensuring that the present methodology is fully effective to inhibit biofilm at the distal region of the catheter.

In some embodiments, it may be desirable to include a means for imparting radioopacity to the catheter body to enable visualization of the implanted catheter using medical imaging technology, particularly if there is a need for such imaging and the components and composition of the implanted catheter are not otherwise sufficiently radioopaque. Radioopacity is required in numerous imaging techniques involving catheter placement and maneuvering, including, by way of example, X-ray, MRI, CT technology, fluoroscopy, or the like. For instance, with a gold electrode, the gold itself will add some radioopacity, but the levels may not be sufficient for the surgeon to visualize under fluoroscopy. If a gold or silver electrode is used, it will generally be desirable for an additional means for imparting radioopacity. This can be done by adding individual markers, like bands, at discrete points along the catheter (not ideal since the physician needs to visualize the cut distal tip of the catheter). Other methods for imparting additional radioopacity to the catheter include the incorporation of radioopaque material into the polymeric insulator alone and/or into the polymer electrode matrix. Examples of suitable radioopaque materials for use in the present context include, without limitation, barium sulfate, barium titanite, zirconium oxide, and bismuth. Titanium, tungsten, or tantalum are also possibilities, providing that the amount incorporated is not so high as to limit conductivity. The radioopaque material can be incorporated into the implantable catheter as (1) strips down the length of the catheter or (2) markers in the form of rings or bands along the catheter. The radioopaque material can also be present as (3) an outer layer completely surrounding the catheter radially as well as continuously along the entire length of the catheter. For (1), radioopaque strips can be co-extruded or painted on via powder mixed in with a polymer in another line or in the form of a polymer/radioopaque maste introduced into another line. For (2), the markers can simply be painted on. For (3), the radioopaque material can be added in powder or paste form to an extrusion mixture.

It will be appreciated that in the foregoing embodiments, the interior of the catheter may be longitudinally segmented into two or more lumens as necessary for implementation in a particular medical procedure. For example, one lumen may be sized to receive a guidewire to facilitate proper and exact positioning of the catheter and particularly the distal tip within the patient's body, as may be confirmed during insertion using fluoroscopy (alternatively, the guidewire can be contained in a single-lumen catheter as illustrated in the figures described above). A second lumen may be used to contain an optical fiber used in any of a variety of contexts, including as a means to measure oxygen concentration in the blood.

In any of the foregoing embodiments, the catheter electrodes and catheter body may be coated with a biocompatible hydrophilic material that reduces surface roughness and decreases the risk of thrombogenicity. Such materials will be known to those of ordinary skill in the art and/or are described in the pertinent texts and literature; see, e.g., LaPorte, *Hydrophilic Polymer Coatings for Medical Devices* (CRC Press, 1997). Several representative examples of suitable coatings include poly(hydroxyethyl methacrylate) (PHEMA); other acrylate polymers and copolymers including poly(hydroxyethoxyethyl methacrylate) (PHEEMA), poly(hydroxydiethoxyethyl methacrylate) (PHDEEMA), poly(methoxyethyl methacrylate) (PMEMA), poly(methoxyethoxyethyl methacrylate) (PMEEMA), poly(methoxydiethoxyethyl methacrylate) (PMEEMA), poly(methoxydiethoxyethyl methacrylate) (PMDEEMA), and poly(ethylene glycol dimethacrylate) (PEGDMA); poly(vinyl alcohol) (PVA); poly(carboxylic acids) such as poly(acrylic acid) (PAA) and poly(methacrylic acid) (PMAA); poly(N-vinyl-2-pyrrolidone); and cellulose ethers such as hydroxypropyl methylcellulose (HPMC) and carboxymethyl cellulose (CMC). Coating thickness is generally in the range of 1 micron to about 15 microns, typically on the order of 2 to 5 microns.

As noted earlier herein, and as will be appreciated by those of ordinary skill in the art, one electrode in the implantable catheter system serves as an anode and another electrode serves as a cathode, as determined by the polarity of the applied voltage. Upon application of a voltage across the electrodes, reactive oxygen species (ROS), i.e., chemically reactive molecules containing oxygen that are destructive to biofilm cells, are formed at both anode and cathode. The reactions taking place at the anode involve the oxidation of anions, particularly chloride ions, which, as noted above, are present throughout the body in the form of dissolved chloride salts. The resulting oxidation products include hypochlorous acid (HOCl) and hypochlorite ion (ClO$^-$), both of which serve as reactive oxidizing agents for purposes of biofilm destruction and growth inhibition. The reactions taking place at the cathode that give rise to oxidizing species include the reduction of endogenous oxygen to give superoxide ion ($O_2^-$), an oxidizing agent, which in turn reacts with water to yield hydrogen peroxide and the peroxide anion.

Although all the aforementioned reactive oxygen species are destructive to biofilm cells, the inventors herein have found that the rate and extent of biofilm destruction is greater at the anode. Accordingly, in a preferred embodiment the methods herein involve periodically reversing the polarity of the applied voltage such that each electrode is alternately an anode or a cathode. In this way, the rate and extent of biofilm destruction is approximately the same at each electrode. Polarity reversal can be manual or automatic, using any effective means for accomplishing the reversal, e.g., using a simple manual switch on the voltage source/power supply or using a programmable automated system in which an automatic controller operates a switch at regularly programmed intervals. Polarity reversals can be of any frequency, e.g., a frequency in the range of about 1 cycle every 30 seconds to about 1 cycle every hour, preferably in the range of about 1 cycle every minute to about 1 cycle every 45 minutes, and more preferably in the range of about 1 cycle every 5 minutes to about 1 cycle every 30 minutes, with "cycle" referring to the interval between polarity reversals in which the direction of current remains constant.

When polarity reversal is automated, as is the case in the preferred embodiment herein, the means for reversing polarity comprises a control circuit that connects the voltage source to the electrodes on the catheter, and not only controls polarity reversal but can also modulate the voltage level, frequency, time of voltage application, current density, and the like, and ideally can be programmed with a predetermined operating profile such as the prevention, destruction, and sensing profiles discussed in Section IV.

III. Manufacture

A variety of techniques can be used to fabricate the implantable catheters of the invention. Suitable manufacturing techniques include electroless plating (also known as chemical plating or auto-catalytic plating), extrusion, chemical vapor deposition (CVD), and printing. All of the aforementioned techniques may be used to provide external electrodes, while electroless plating and extrusion are the methods of choice for manufacture of implantable catheters having both inner and outer electrodes.

As will be appreciated in the art of electrode fabrication, electroless plating is a widely used non-galvanic plating method for providing an electrically conductive material on substrates, including insulating substrates, which, in the context of the present invention, involves the creation of thin-film electrodes on the catheter surface or surfaces. Electroless plating involves several simultaneous reactions in aqueous solution, which occur without the use of electrical power as in electroplating. Accordingly, fabrication of electrodes in the present method using the electroless plating technique involves first activating the exterior and interior surfaces of the catheter by treating the surfaces with an activating agent that will covalently or electrostatically bind the metal to be deposited. With a silicone catheter, this activation layer, or "seed layer," is readily provided using a silanizing agent that reacts with surface silanol groups and results in free reactive moieties on the catheter surface. The reactive surface moieties may be, for instance, sulfhydryl, cyano, or amino, depending on the silanizing agent selected. Representative silanizing agents include, without limitation, (3-aminopropyl)-trimethoxysilane (APTMS) and (3-mercaptopropyl)-trimethoxysilane (MPTMS). Following surface activation, the activated surfaces of the catheter are brought into contact with a metallic compound or composition, generally composed of a noble metal that is inert but provides an electrochemically active surface, which serves as the substrate for plating. Examples of noble metals include gold, silver, palladium, and platinum.

Figure 6:
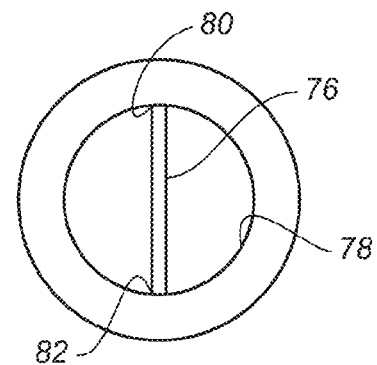
FIG. 6 illustrates the use of an interior mask in electrode fabrication via electroless plating, to create the interior gaps seen in the embodiment of FIG. 5.

An exemplary process is as follows. Prior to surface activation, the regions of the catheter surfaces that will not be plated, i.e., the regions that will serve as the gaps between electrodes, are masked. This can be done by using any material that is impermeable as well as inert to the electroless plating solutions, with the interior gap provided by physically introducing an elongate rigid mask material (e.g., a rigid piece of plastic) into the catheter and the exterior gap provided using exterior masking segments. As illustrated in FIG. 6, the interior masking segment 76 extends across the inner diameter of the inner catheter surface 78 from one interior section 80 to the diametrically opposed interior section 82. Continuing with the exemplary process, the catheter is immersed in an aqueous solution of palladium chloride and then coated with a solution containing a stannous salt (e.g., stannous chloride), generally by immersion in that solution. This process, as is well known in the art, results in deposition of Pd$^0$, palladium metal, on the catheter surface. The interior masking segment 76 is then extracted from the catheter interior, while exterior masking segments are simply physically removed from the exterior catheter surface. At this point, one can deposit gold or an alternative metallic electrode material onto the palladium-coated regions of the catheter surfaces using any plating technique, to provide a thin film electrode layer in the range of about 50 nm to about 100 nm in thickness.

Another method for binding a metallic material to the catheter surface is to deposit a metal precursor in a solvent on the surface, evaporate the solvent, and then convert the metal precursor to active metal. For instance, the metal precursor solution may be a solution of a palladium compound and a Lewis base ligand in a solvent, e.g., palladium propionate, propionate acetate, etc., and a nucleophilic nitrogenous ligand such as aniline, pyridine, cyclopentyl amine, or the like. After deposition, the solution is exposed to conditions that promote evaporation of the solvent, e.g., heat or convection. The coating is then treated in a manner that chemically facilitates separation of the ligand from palladium, leaving a layer of elemental palladium on the catheter surface. Such processes are described in detail in U.S. Pat. No. 7,981,508 to Sharma et al. (assigned to SRI International, Menlo Park, Calif.), the disclosure of which is incorporated by reference herein.

The advantages of electroless plating are that the reactions involved are very simple electrochemical reactions that take place on a surface and proceed at ambient temperature with aqueous solutions. There is no need for elevated temperature or pressure, organic solvents, or complex equipment. It should also be noted that in the present context, fabrication of the implantable catheter using electroless plating is a versatile manufacturing technique, insofar as the process can be used for providing exterior electrodes only, interior electrodes only, or both interior and exterior electrodes.

Another method for fabricating the implantable catheters of the invention involves extrusion using extrusion techniques that are known in the art. In this embodiment, a paste is prepared using a precursor or prepolymer to the flexible elastomer that will serve as the catheter body, and, on the exterior and optionally the interior of the paste as it is fed into the extruder, at least two strips of a conductive electrode composition. The precursor or prepolymer to the flexible elastomer is cross-linkable with heat, ultraviolet radiation, or chemically, using a cross-linking agent. The conductive electrode composition comprises a mixture of conductive particles, e.g., carbon particles, and a thermosetting or thermoplastic, preferably thermosetting polymer that is curable photochemically, thermally, or chemically, e.g., in the presence of moisture. With silicone catheters, as an example, the paste would contain a crosslinkable siloxane polymer or prepolymer that is readily curable, to form the catheter body. Depending on the crosslinkable siloxane polymer or prepolymer, an added crosslinking agent might be necessary. As used herein, the term "crosslinkable" refers to a polysiloxane having reactive or functional groups that enable thermal, photochemical, or chemical crosslinking Silicone polymers of this description are generally known and commercially available. By way of illustration, mention may be made of dimethyl polysiloxane, methylphenyl polysiloxane, cyanoalkylmethyl polysiloxane, and fluoroalkylmethyl siloxane. A particularly preferred crosslinkable polysiloxane is dimethyl polysiloxane, which is characterized as possessing high strength and elasticity. The conductive electrode composition is preferably composed of a mixture of particulate carbon, e.g., carbon powder, carbon nanoparticles, carbon fibers, or the like, and a thermosetting polymer, e.g., a thermally or photochemically curable polymer typically selected from polyurethanes, polyvinyl chloride, silicones, poly(styrene-butadiene-styrene), and polyether-amide block copolymers, with carbon representing in the range of about 5 wt. % to about 25 wt. % of the mixture. The extruded catheter is then treated as necessary, e.g., with light and/or heat and/or moisture, to cure the polysiloxane and thereby form the catheter body and to harden the thermosetting polymer of the conductive electrode composition to form the carbon-polymer composite electrodes. With catheters fabricated from extrudable materials other than silicone, a similar manufacturing process would be used.

In some embodiments, the material to be extruded can be heated prior to and/or during the extrusion process. Electrode structures having a first conductive material, a second conductive material, and a dielectric material can be coextruded in this manner to provide an electrode structure having the first conductive material and the second conductive material electrically isolated by the dielectric material.

Because extrusion is a simple and straightforward technique, and makes it possible to carefully control the position, width, and thickness of the electrodes, it is a preferred technique for fabrication of the implantable catheter.

As noted above, the implantable catheter can also be fabricated by depositing electrode material on the exterior surface of a catheter using CVD, or by using a printing technique that essentially involves pressing pre-formed electrode strips into the exterior surface of a softened catheter body.

IV. Operation

The operating parameters suitable for implementation of the present invention will vary, depending on the intended method of use and the voltage application regimen. That is, the method of the invention may be used to kill microorganisms in an existing biofilm on an implantable catheter surface, to prevent growth of a biofilm on an implantable catheter surface, or to sense the formation of a biofilm on an implantable catheter surface. In addition, the electric field generated on the catheter surface(s) may be applied by the voltage source either intermittently or continuously.

Initially, then, when the method is implemented to kill microorganisms in an existing biofilm, and the electric field is generated intermittently, the following operating parameters generally apply: a duration of voltage application in the range of about 15 minutes to about 6 hours, typically in the range of about 30 minutes to about 3 hours; application frequency in the range of about once or twice daily to about once or twice weekly; an applied voltage in the range of about 0.5 V to about 1.5 V, preferably in the range of about 0.6 V to about 1.2 V, most typically in the range of about 0.8 V to about 1.2 V; and a current density in the range of about 5 $\mu A/cm^2$ to about 200 $\mu A/cm^2$, typically in the range of about 10 $\mu A/cm^2$ to about 200 $\mu A/cm^2$, and most typically in the range of about 20 $\mu A/cm^2$ to about 100 $\mu A/cm^2$. It will be appreciated that operating at a higher current density reduces the duration of voltage application, and that operating at a lower current density increases the required duration of voltage application. Generally, however, the foregoing parameters apply using intermittent application with the intention of destroying an existing biofilm. Intermittent application may be desirable in contexts where there are numerous patients with implanted catheters, e.g., in a hospital setting, and in which the number of available voltage sources may be limited.

When the method is implemented to kill microorganisms in an existing biofilm and the electric field is generated continuously, however, somewhat lower voltage is applied for a longer time period, where typically this extended time period is at least 72 hours, and often for several weeks or even several months or more. Generally, the applied voltage is in the range of about 0.3 V to about 1.3 V, typically in the range of about 0.3 V to about 0.7 V, and the current density is in the range of about 5 $\mu A/cm^2$ to about 50 $\mu A/cm^2$.

In preventing the formation of a biofilm on an implantable catheter, application of voltage to generate an electric field across the catheter surface(s) is preferably an ongoing, continuous, low voltage process, with applied voltage in the range of about 0.2 V to about 1.0 V, preferably in the range of about 0.3 V to about 0.6 V. The resulting current density at the catheter surface is typically in the range of about 5 $\mu A/cm^2$ to about 30 $\mu A/cm^2$.

The invention also encompasses a method and system for sensing the formation of or confirming the presence of a biofilm on an implantable catheter surface, and the application of voltage to generate an electric field across the catheter surface may be intermittent or continuous. Very low voltage is required here, on the order of about 10 mV to about 30 mV. In one embodiment, the system includes a means for detecting an increase in impedance across the external electrodes on the outer surface and/or inner surface of the catheter, i.e., an increase relative to the measured impedance across the electrodes in the absence of a biofilm. The detection means, e.g., Electrical Impedance Spectroscopy (EIS) or an alternative technique, is operatively connected to a means for communicating the measurement to an external device for a user to view. The communication means comprises electric circuitry for providing an output signal, e.g., an electronic, optical, or electromagnetic signal, indicative of measured impedance. Generally an increase in impedance of more than 50% noted in at least two consecutive measurements is indicative of the presence of or formation of a biofilm on the catheter surface. Once it appears that a biofilm has been detected, one of the above methods for killing microorganisms within the biofilm may be implemented using the same system and voltage application device to ensure that the implanted catheter is disinfected.

It should be emphasized that the electrodes used for biofilm destruction, i.e., for killing microorganisms in the biofilm, can be used for biofilm sensing as well employing the aforementioned impedance measurement technique. As a result, the sensing process can be employed initially to detect changes in impedance associated with the growth of a pathogenic biofilm, and as noted above, the same system, without modification or adaptation of any sort, may then be activated at a higher voltage, as described earlier herein, to kill microorganisms in the biofilm and thereby disinfect the catheter surface.

In a related embodiment, rather than use impedance measurement to detect the presence or formation of a biofilm on the catheter surface, an electrochemical or other type of oxygen measurement may be made at the catheter surface, as biofilm growth tends to substantially deplete oxygen. In fact, it has been reported that under a biofilm that is only about 70 microns in thickness, the oxygen in the region can be entirely depleted. See Ganesh et al. (2008) *Optics and Lasers in Engineering* 46:321-327. Once a user has determined that the oxygen level has dropped significantly at the catheter surface, the microorganisms in the biofilm can be killed using the method described earlier herein.

Any electrochemical oxygen sensor and oxygen determination method may be used, including, by way of example, a galvanic oxygen sensor, a polarographic oxygen sensor, a coulometric sensor, or the like.

Ideally, the information pertaining to actual use of a single implantable catheter system in a patient can be stored and tracked. Such information includes, for example, the installation date of the catheter, the access dates of the catheter, the activation dates and times, voltage levels, duration of use, and the like. Information on the activation pattern of a catheter, e.g., prophylactic at a low voltage level versus activation at a high level once a biofilm has been detected, can yield critical information relevant to a determination of what therapies work best for which patients. To enable gathering of the aforementioned information, the implantable catheter system should include an internal clock that can store date and time, a sensor (e.g., a capacitive or resistive sensor) in the catheter to determine when its fluid connector is accessed, a means for monitoring activation patterns and power used, and a means to communicate with a data output device and optionally through a wired or wireless communication channel with a hospital network. The pertinent information can thereby be made known to medical personnel through a dashboard, the patient's electronic medical record (EMR) or a parallel system or application. The information provided will serve as a quality control for the use of the catheter and a source of new knowledge to optimize the clinical use of the catheter and reduce the morbidity and mortality due to biofilm infections. More specifically, the information system will provide the following benefits: provide control over the number of times the implantable catheter is accessed and the length of time it is used; produce new knowledge to determine what pattern of use results in better outcomes for a patient; avoid unnecessary and costly removal of catheters when catheter infection is suspected; and over time, optimize the use of activation patterns of the catheter so as to result in optimal patient outcomes.

V. Utility

The implantable catheter of the invention finds utility in a diverse plurality of contexts in which a catheter is implanted in a patient. In general, the method and implantable catheter of the invention find utility in connection with a wide variety of catheter types, e.g., with arterial catheters, central venous catheters, dialysis tubing, endotracheal tubes, enteral feeding tubes, Foley catheters, gastrostomy tubes, hemodialysis catheters, nasogastric tubes, nephrostomy tubing, pulmonary artery catheters, tracheostomy tubes, tympanostomy tubes, shunts, umbilical catheters, urinary catheters, and the like. Generally preferred catheter types are short-term and long-term indwelling catheters, with short-term catheters remaining in place for less than 30 days, and long-term catheterization defined as requiring implantation for more than 30 days.

Particularly important areas of use are medical procedures that require repeated and prolonged access to a patient's vascular system, for example, to carry out transfusions, administer antibiotics, drugs, nutrition, or chemotherapy agents to the bloodstream, or to purify a patient's blood. For example, central venous catheters normally remain implanted for a longer period of time than other venous catheters, especially when there is an extended and ongoing need for their use, such as the administration of total parenteral nutrition in a chronically ill patient. As another example, during treatment of diabetic patients, blood is removed for filtering and purification externally to the body; typically, access is obtained through a vein or artery.

Cumulative damage to the skin and vascular walls caused by repeated punctures makes it impractical to introduce a new catheter into the patient's venous system at regular intervals. Use of the implantable catheter of the invention eliminates the need for repeated removal and insertion of catheters, as the infecting microorganisms in biofilms can be killed and the catheter thus disinfected without removal from the patient's body.

In use, then, the implantable catheter is inserted through the patient's skin so that the distal end remains under the skin, within the patient's body, while the proximal end extends outside the body for connection to an external line. The distal end generally enters a patient's vein, and the proximal end is connected through an external line to a device used to receive, supply, and/or process medical fluids, such as blood. The outer surface of the catheter body is exposed to the environment surrounding the catheter. For example, the outer surface may be in contact with the contents of a body lumen into which the catheter has been inserted.

It will be appreciated by those skilled in the art that the invention described herein can be implemented in a range of contexts in which a device is implanted in the body of a patient, in which case the implant surfaces are at risk for infection with biofilm microorganisms. Such implants include, without limitation, stents, including biliary, hepatic, and esophageal stents, orthopedic prostheses, pins, joints, and other implants, dental implants, intracardiac prostheses, vascular prostheses including prosthetic heart valves, artificial hearts, and pacemakers.

EXPERIMENTAL

Materials and Methods

Strains and Growth Conditions:

Throughout the study *Pseudomonas aeruginosa* (PAO1) tagged with green fluorescent protein (Gfp) and the characteristics described in Table 1 was used. In a few experiments *E. coli* and *Staphylococcus aurous* bacterial strains as also listed in Table 1 were used. Strains were grown in M9 media with addition of 1 mM $MgCl_2$, 0.1 mM $CaCl_2$, and 0.01 mM $FeCl_3$. Media were adjusted to physiological/blood stream NaCl concentrations of 0.9%. In addition, 1 mM glucose was added as the sole carbon source for batch experiments, and 0.01 mM glucose was added for flow chamber experiments. For *Staphylococcus aureus* trypticase soy broth (TSB) was used as growth media. When required, antibiotics were added at final concentrations of 100 μg/ml Ampicillin and 20 μg/ml Gentamycin. Visualization of live and dead cells was carried out by staining with Baclight live dead stain from Molecular Probes, Inc. (Eugene, Oreg., USA) showing live cells by green fluorescence and dead cells by red fluorescence. When Gfp was constitutively expressed in cells (e.g., for PAO1), live cells are represented by green fluorescence from Gfp.

TABLE 1

| Strain | Relevant characteristics |
| --- | --- |
| *Pseudomonas aeruginosa* (PAO1) | Tn7::Gfp tagged, $Amp^r$, $Km^r$ |
| *E. coli* (Sar18[pAR108]) | Plasmid Gfp tagged, $Amp^r$ |
| *Staphylococcus aurous*(1) | RN8325-4, mutation in Rsb, sigmaB- |
| *Staphylococcus aurous*(2) | 15981 |

Flow Chamber Experiments:

Biofilms were grown at 30° C. in three channel flow chambers with individual channel dimensions of 1×4×40 mm. The flow system was assembled and prepared as described by Christensen et al. (1999) *Methods Enzymol.* 310:20-42, and Sternberg et al. (January 2006) *Curr. Protoc. Microbiol.* January; Chapter 1: Unit 1B.2. The substratum consisted of a microscope glass coverslip (st1; Knittel Glaser, Braunschweig, Germany) mounted with a gold anode and cathode grid. Each channel was supplied with a flow of 3 ml/h of M9-medium containing the appropriate carbon source. Flow cells were inoculated with the strain of interest grown for 18 h in LB medium and diluted to OD 0.01 prior to inoculation. After having stopped the media flow the flow channels were inverted and 250 μl of the diluted mixture was carefully injected into each flow channel using a small syringe. After 1 h the flow channel was inverted and the flow was resumed using a Watson Marlow 205S peristaltic pump (Watson Marlow Inc., Wilmington, Mass.). The mean flow velocity in the flow cells was 0.2 mm/s. A scaled up flow cell was developed and used for monitoring growth and killing efficiencies on typical catheter-length electrodes. This flow cell had the dimensions of 4×30×160 mm and was mounted with graphite electrodes. In order to follow the killing of cells using applied electrochemistry vis-à-vis the spatial localization of single cells and biofilm developed in the flow channels, cells were stained with live dead stain 15 min prior to inspection using confocal microscopy.

Two Biofilm Systems:

Throughout these studies, a static system was used in which graphite electrodes (4 cm length) were mounted on the bottom of 6 well Petri dishes, with inspection taking place directly in the well using dipping lens objectives. In this system, biofilms were allowed to develop for 6 h. This system allowed for development of a thin monolayer biofilm at the substratum with beginning small micro colony structures. A second system used was a flow system that allowed for mature biofilm development over several days and treatment at different time points during biofilm maturation. In both systems, it was possible to perform treatment on established biofilms and perform prevention of biofilm development by applying electrochemistry from initial attachment of cells to electrode surface.

Microscopy and Image Analysis:

All microscopic observations and image acquisition was performed on a TCDSP2 scanning confocal laser microscope, CLSM (Leica Lasertechnik GmbH, Heidelberg, Germany) equipped with an argon/krypton laser and detectors and filter sets for simultaneous monitoring of Syto9/Gfp (excitation 488 nm, emission 517 nm) and propidium iodide (excitation 543 nm, emission 565 nm). Images were obtained using a 63×/1.4 Plan-APOChromat, a 63×/0.90 w HCX-APO and a 20×/0.50 w HCX-APO objective. Multichannel simulated fluorescence projection (SFP, a shadow projection) images and vertical cross sections through the biofilm were generated by using the IMARIS software package (Bitplane AG, Zurich, Switzerland). Images were further processed for display by using Photoshop software (Adobe, Mountain View, Calif.).

Image Acquisition for Quantification using COMSTAT:

For quantification of biomass and calculation of % of dead cells, independent biofilm experiments were performed acquiring image stacks randomly of the respective biofilm samples. Images were further treated using COMSTAT (Heydorn et al. (October 2000) *Microbiology* 146 (Pt 10):23950407. By viewing the images from the confocal microscope and quantifying the relative amounts of green cells and red cells at regular intervals, one can calculate biomass and monitor biofilm growth. The fraction of dead cells can thereby be deduced throughout the electrochemical process.

Results

The images obtained using confocal microscopy and shown in FIGS. 7-15 and 17 confirm the efficacy of the electrochemical method and system of the invention in inhibiting biofilm growth, in terms of both killing microorganisms and preventing biofilm growth.

Figure 9B:
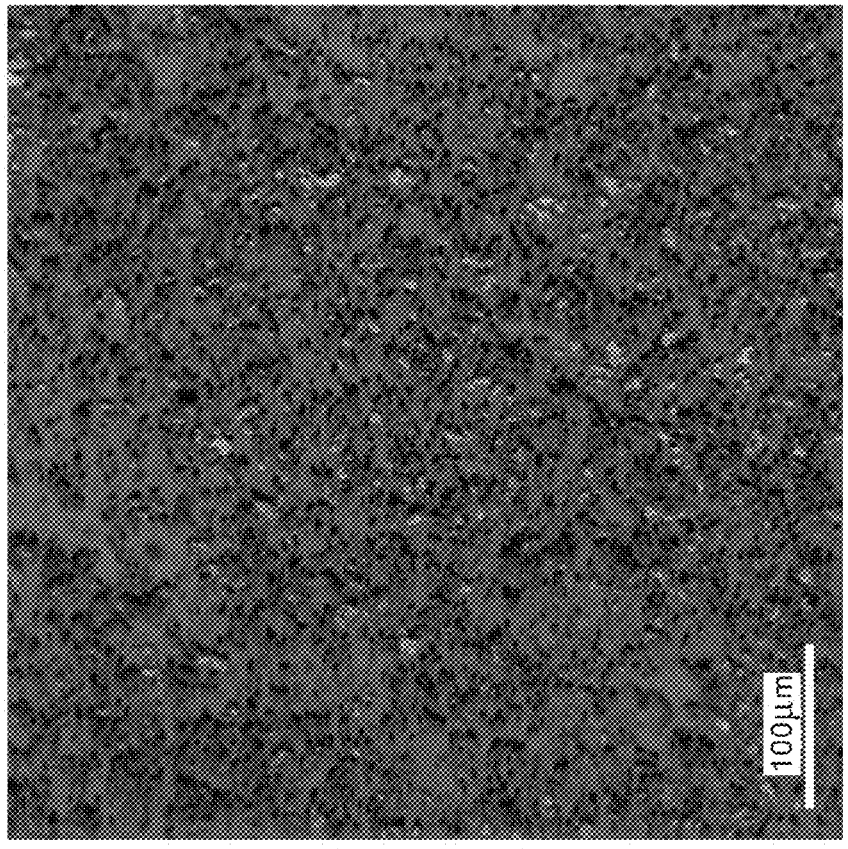
FIGS. 9A and 9B show images obtained using confocal microscopy of a *P. aeruginosa* biofilm grown for 6 h in minimal static media on a graphite electrode (4 cm in length) and exposed to electrochemistry using −0.6 V at 10 µA/cm².
Figure 9A:
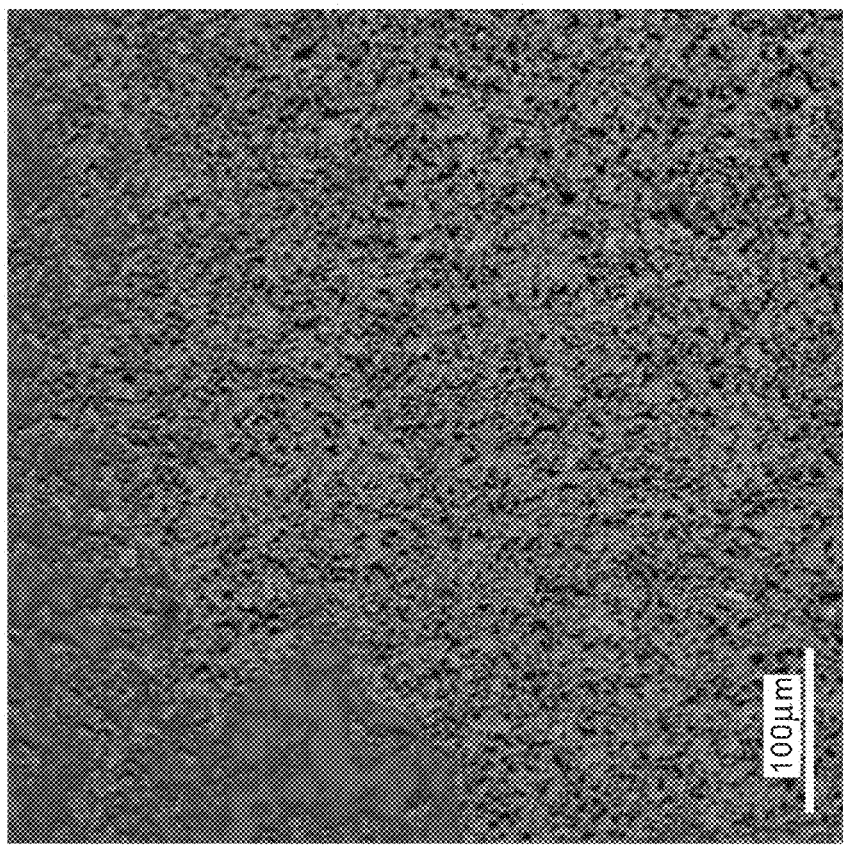
Figure 13B:
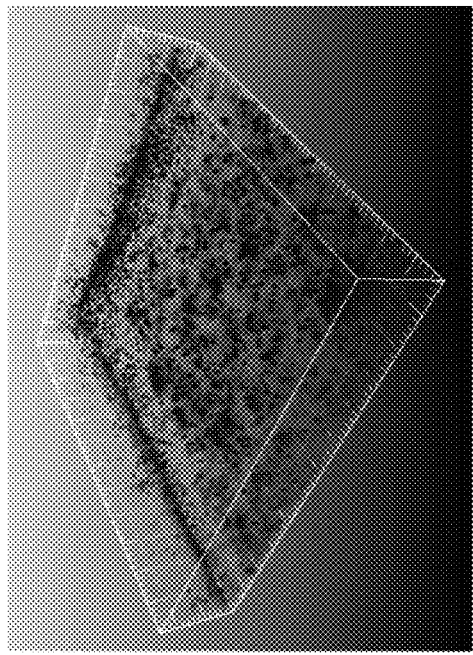
Figure 13D:
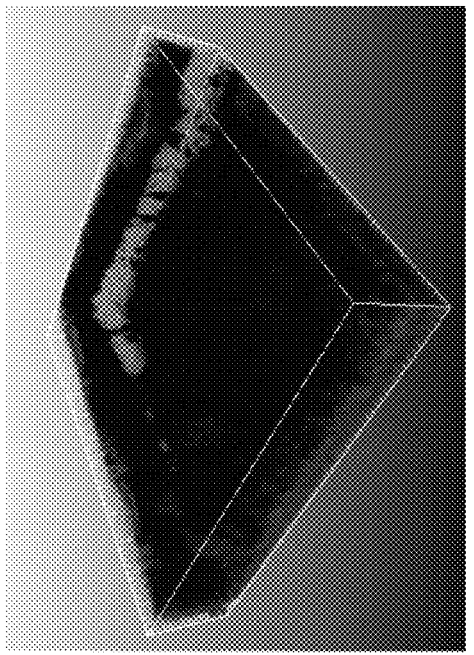
FIG. 13D shows the anode-associated biofilm after 3 h treatment.
Figure 13A:
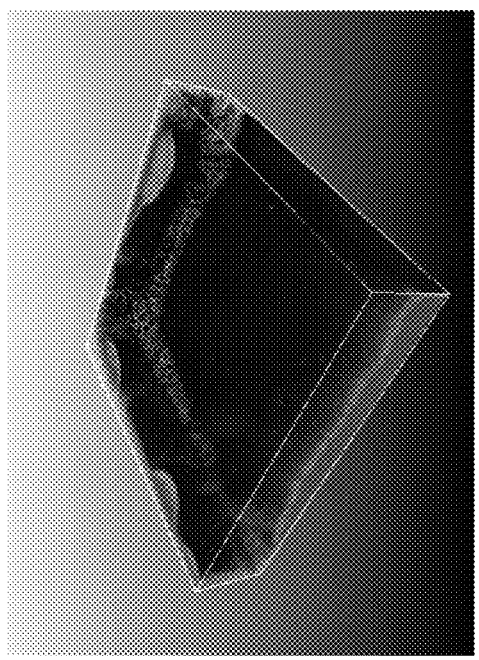
FIG. 13A shows the anode before electrochemical treatment.
Figure 13C:
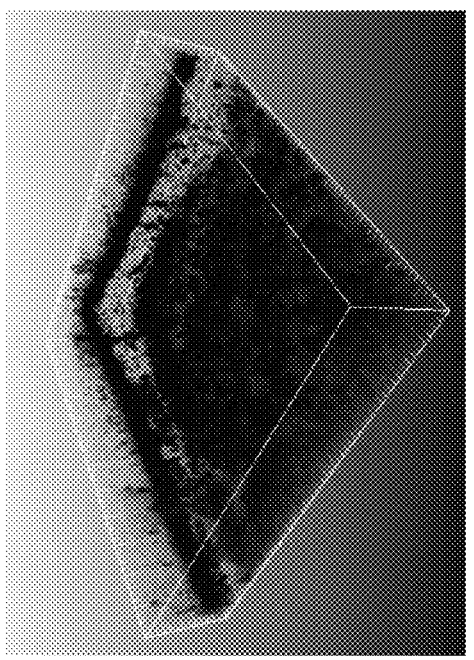

FIGS. 7-11 show images of *P. aeruginosa* biofilms grown in the static system, in glucose minimal media, on a 4 cm long graphite electrode (FIGS. 7-9 and 11) or on a 16 cm long graphite electrode (FIG. 10). These images were taken 4 cm and 12 cm from the electrode connection to the power supply respectively, and varying electrochemical treatments were used, as follows: FIG. 7, −1.2 V at 20 $\mu A/cm^2$; FIG. 8, −0.6 V at 10 $\mu A/cm^2$; FIG. 9, −0.6 V at 10 $\mu A/cm^2$; FIG. 10, −1.2 V at 25 $\mu A/cm^2$; and FIG. 11, −0.8 V at 25 $\mu A/cm^2$. With the live cells represented in green from Gfp inserted into the cells and dead cells shown in red after propidium iodide staining, it is clear that the method and system of the invention have a significant effect in inhibiting biofilms (with respect to killing and biofilm biomass) regardless of electrode length and using a range of electrochemical parameters.

Figure 15:
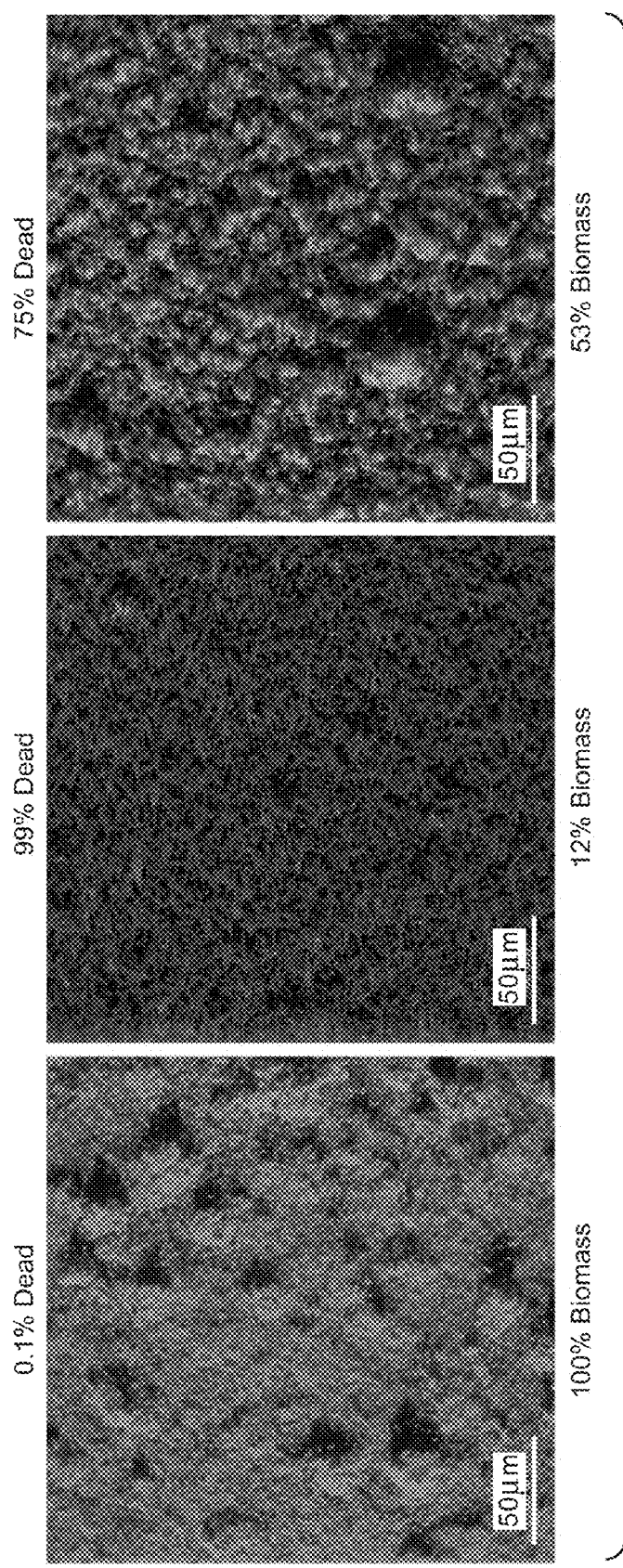
FIG. 15 shows images obtained using confocal microscopy of a *P. aeruginosa* biofilm grown in glucose minimal media for 72 h in flow chambers on a 20 cm long graphite electrode, and exposed to electrochemistry using 20 µA/cm$^2$.
Figure 16:
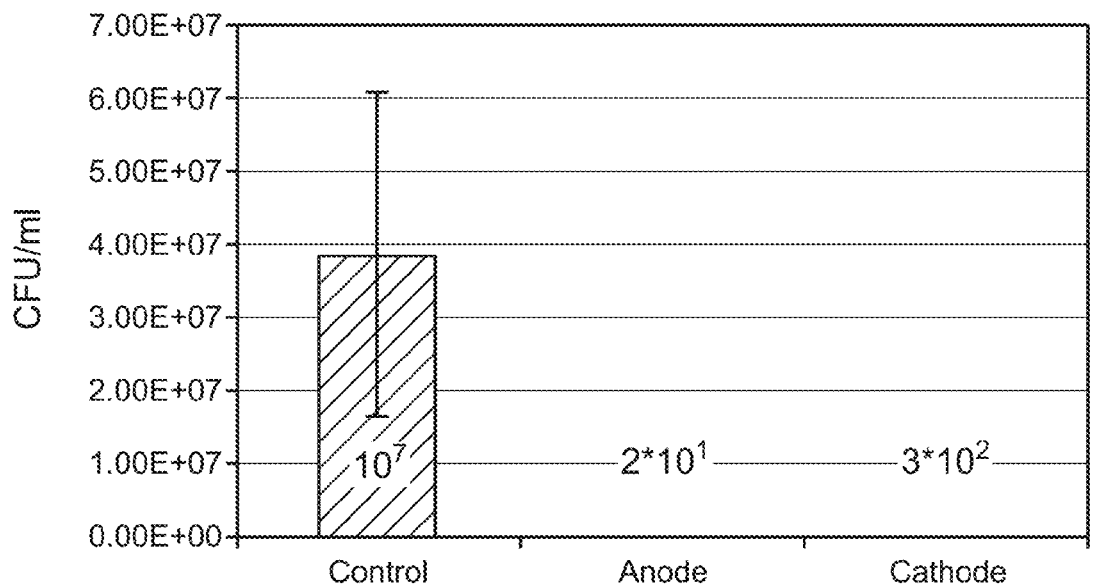
FIG. 16 is a column diagram showing CFU/ml of isolated cells from Gfp tagged *P. aeruginosa* biofilm grown in glucose minimal media on graphite electrode. Biofilm was exposed to electrochemistry using 10-25 µA/cm$^2$. Biofilm cells were isolated from graphite electrode before (Control) and after treatment (Anode and Cathode) followed by plating for determination of CFU/ml on selective plates. The X-axis shows Control, Anode and Cathode, respectively. The units on the Y-axis are CFU/ml.

FIG. 12-15 show images of *P. aeruginosa* biofilms grown in a dynamic, flow-through system using the flow chambers described earlier herein. Again, the images confirm the efficacy of the invention in a variety of contexts: duration of biofilm growth (FIG. 12, 24 h; FIGS. 13-15, 72 h); type of electrode (FIGS. 12 and 13, gold on glass; FIGS. 14 and 15, a 20 cm graphite electrode); and electrochemical parameters (FIGS. 12 and 13, −1.2 V at 20 $\mu A/cm^2$; FIG. 14, 2 $\mu A/cm^2$; FIG. 15, 20 $\mu A/cm^2$). FIG. 16 show killing efficacy of *P. aeruginosa* biofilms evaluated by colony forming units (CFU/mL) after electrochemical treatment according to the invention.

Figure 20A:
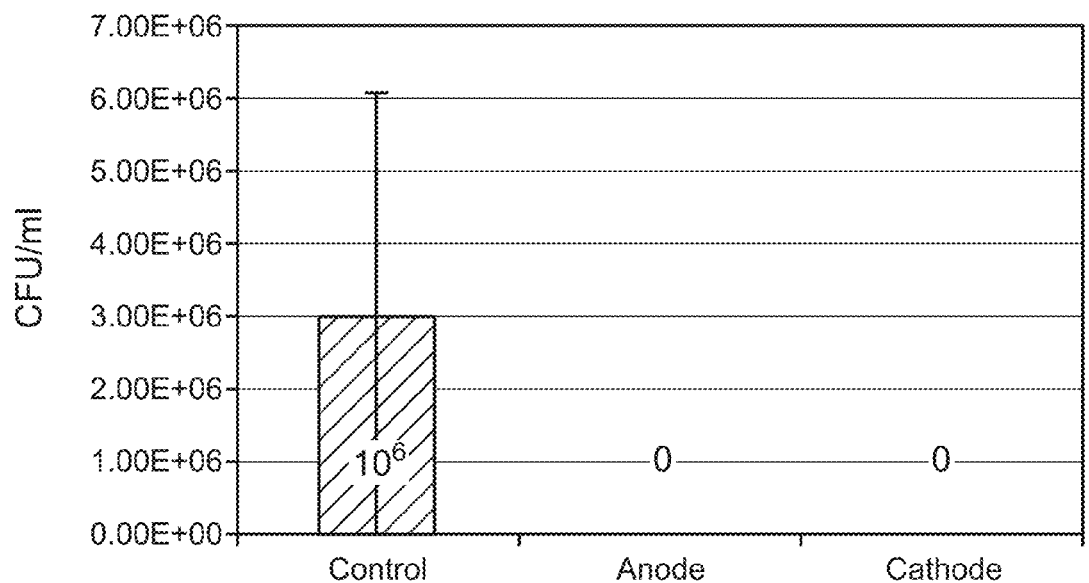
FIGS. 20A and 20B show a column diagram showing CFU/ml of isolated cells from *Staphylococcus aurous* [RN8325-4].
Figure 20B:
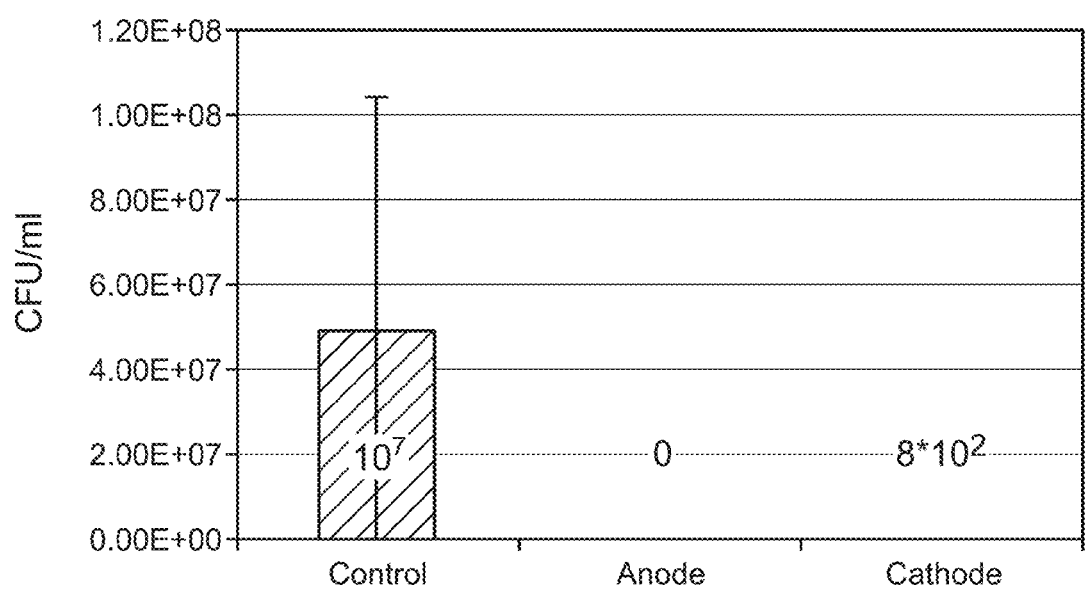

FIGS. 17, 18, 19 and 20 illustrate efficacy with additional microorganisms, *E. coli* (images shown in FIG. 17 and a CFU/ml diagram shown in FIG. 18) and *Staphylococcus* aurous strains (images shown in FIG. 19 and a CFU/ml diagram shown in FIG. 20).

Figure 18:
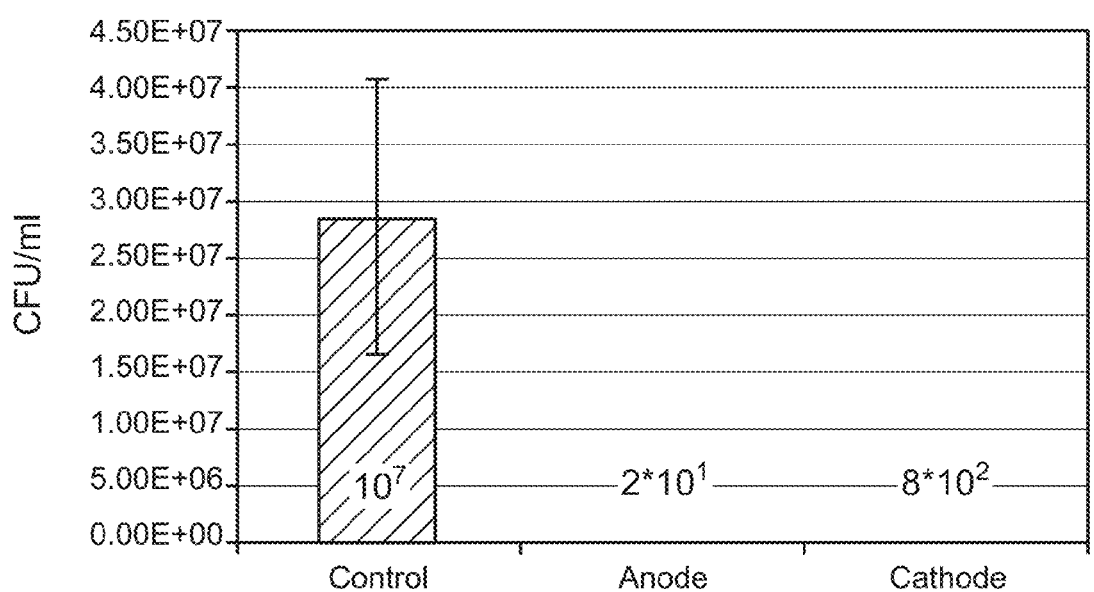
FIG. 18 is a column diagram showing CFU/ml of isolated cells from *E. coli* biofilm grown in glucose minimal media on graphite electrode. Biofilm was exposed to electrochemistry using 10-25 µA/cm$^2$. Biofilm cells were isolated from graphite electrode before (Control) and after treatment (Anode and Cathode) followed by plating for determination of CFU/ml on selective plates. The X-axis shows Control, Anode and Cathode, respectively, and the units on the Y-axis show CFU/ml.
Figure 19C:
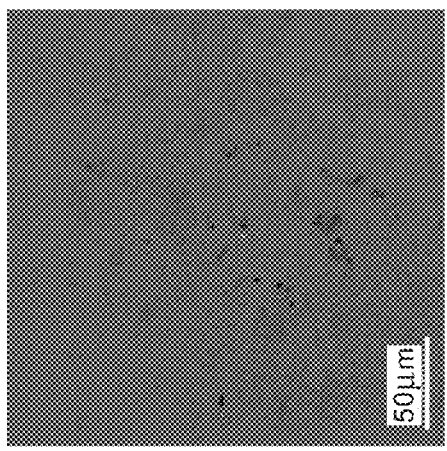
FIGS. 19A, 19B, 19C, 19D, 19E, and 19F show a biofilm of *Staphylococcus aurous* [RN8325-4] (having a mutation in RsbU, which makes this strain sigma B negative; sigma B regulates many virulence factors in *S. aureus*) (A, B, C) and *Staphylococcus aurous* [15981] (expressing virulence) (D, E, F) cells grown for 6 h in TSB media on a 4 cm long graphite electrode. Images were obtained 4 cm from the electrode connection to the power supply. The biofilm was exposed to electrochemistry using −0.8V (25 µA/cm$^2$). A and D show the biofilm on the graphite electrode without treatment, while B and E show the anode-associated biofilm after 1 h treatment and C and F show the cathode after 1 h treatment.
Figure 19F:
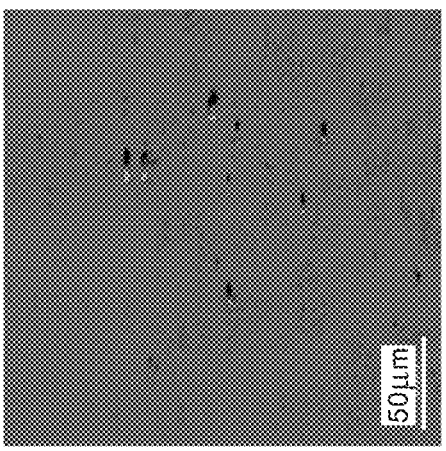
Figure 19B:
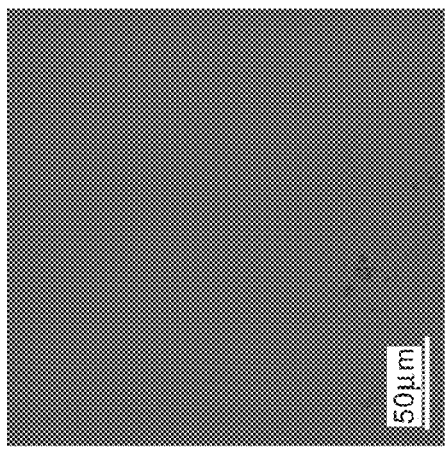
Figure 19E:
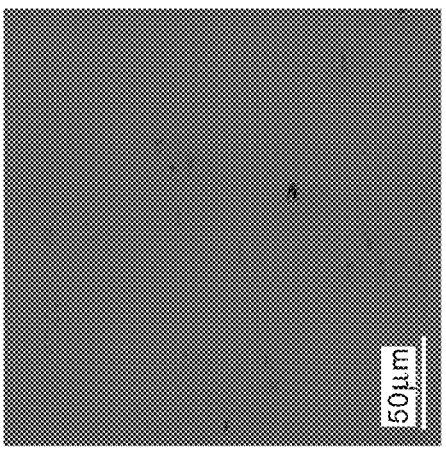
Figure 19A:
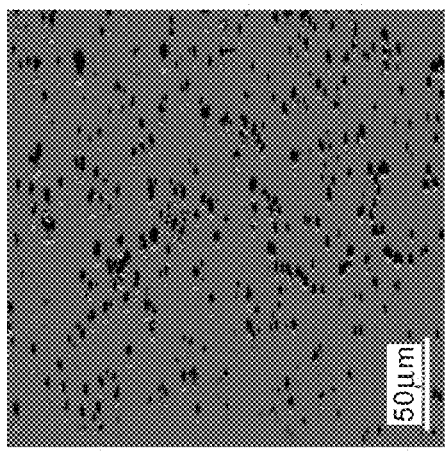
Figure 19D:
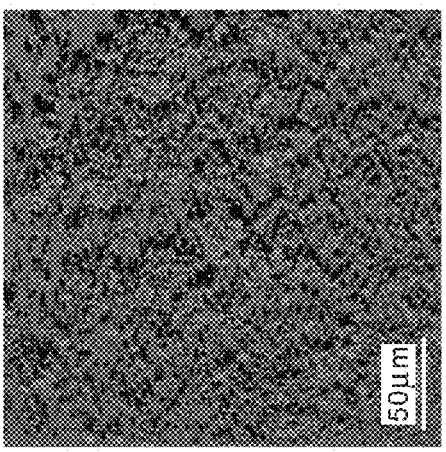

With the live cells represented in green from Gfp inserted into the cells and dead cells shown in red after propidium iodide staining, it is clear from the images obtained as well as the CFU/ml diagrams of FIGS. 16, 18 and 20 that the method and system of the invention have a significant effect in inhibiting/killing biofilms regardless of electrode length and using a range of electrochemical parameters.

The invention claimed is:

1. A method for electrochemically disinfecting a catheter implanted in a patient's body, by creating a biofilm-inhibiting concentration of oxidizing agents, the catheter comprising:
    an elongate catheter body comprising a dielectric material and having a proximal region, a distal region, a lumen extending through the catheter body and adapted to transport fluid from the proximal region to the distal region, an outer surface on the exterior of the catheter body, and an inner surface on the interior of the lumen, and
    at least two exterior electrodes on and integral with the outer surface of the catheter, the exterior electrodes being elongate and extending longitudinally along the outer surface of the catheter body from the proximal region to the distal region, wherein the exterior electrodes extend radially inward from the outer surface through a wall of the catheter body to the inner surface, thereby additionally serving as interior electrodes;
    wherein the two exterior electrodes are separated by a pair of gaps, each gap comprising the dielectric material of the catheter body, and extending radially from the outer surface to the inner surface of the catheter body and longitudinally from the proximal region to the distal region;
    the method comprising, in the absence of an added biocidal agent, with the catheter implanted in the patient's body, and without removing the catheter from the patient's body, applying a voltage across the exterior electrodes of a magnitude that is effective to create a biofilm-inhibiting concentration of oxidizing agents from endogenous compounds present in the body.

2. The method of claim 1 wherein the exterior electrodes comprise an anode and a cathode serving as a working electrode and a counter electrode, and the exterior electrodes further include a third electrode which serves as a reference electrode.

3. The method of claim 1 wherein the catheter body is comprised of a flexible elastomeric material.

4. The method of claim 1 wherein the catheter body is comprised of a flexible elastomeric material comprising silicone, polyurethane, polyvinyl chloride, polyethylene or latex.

5. The method of claim 1 wherein the catheter body is comprised of a flexible elastomeric material comprising silicone or polyurethane.

6. The method of claim 1 wherein the electrodes are metallic.

7. The method of claim 1 wherein the electrodes are comprised of a carbon-polymer composite.

8. The method of claim 1 wherein the electrodes are comprised of a carbon-polymer composite comprising carbon particles and a thermosetting or thermoplastic polymer.

9. The method of claim 1 wherein each gap is in the range of about 1000 Å to about 2 μm.

10. The method of claim 1 wherein each gap is in the range of about 10 μm to about 200 μm.

11. The method of claim 1 wherein the exterior electrodes have a thickness in the range of about 500 Å to about 30 μm.

12. The method of claim 1 wherein the catheter has a plurality of exterior electrodes comprising a plurality of anodes and an equal number of cathodes.

13. The method of claim 1 wherein the catheter is a central venous catheter implanted in a vein.

14. The method of claim 1 wherein the catheter comprises a biofilm present or forming on at least the outer surface of the catheter, and the applying step kills microorganisms of the biofilm.

15. The method of claim 1 wherein the voltage is provided by a voltage source selected from a direct current source, an alternating current source, and a pulsed voltage source, wherein the source is in electrical communication with the electrodes.

16. The method of claim 1 wherein the voltage source is an alternating current source.

17. The method of claim 1 wherein the voltage source is a direct current source, and polarity is alternated throughout an extended time period such that each electrode alternates between functioning as an anode and functioning as a cathode.

18. The method of claim 1 wherein the voltage source is a direct current source, and polarity is alternated throughout an extended time period such that each electrode alternates between functioning as an anode and functioning as a cathode, wherein the polarity is alternated every five to thirty minutes.

19. The method of claim 1 wherein the voltage is provided by a voltage source that is a direct current source in the form of a portable battery pack.

20. The method of claim 1 wherein the voltage is applied intermittently at regular intervals for a time period in the range of about 15 minutes to about 6 hours.

21. The method of claim 1 wherein the voltage is applied intermittently at regular intervals for a time period in the range of about 30 minutes to about 3 hours.

22. The method of claim 1 wherein the voltage is applied continuously for an extended time period of at least 72 hours.

23. The method of claim 1 wherein the voltage is applied continuously for an extended time period of at least 72 hours, wherein the magnitude of the voltage is in the range of about 0.3 V to about 1.3 V.

24. The method of claim 1 wherein the voltage is applied continuously for an extended time period of at least 72 hours, wherein the magnitude of the voltage is in the range of about 0.3 V to about 0.7 V.

25. The method of claim 1 wherein the voltage is applied continuously for an extended time period of at least 72 hours, wherein the magnitude of the voltage is in the range of about 0.2 V to about 1.0 V.

26. The method of claim 1 wherein the voltage is applied continuously for an extended time period of at least 72 hours, wherein the voltage applied results in a current density in the range of about 5 µA/cm² to about 50 µA/cm² on at least the outer surface of the catheter body.

27. The method of claim 1 wherein the magnitude of the voltage is in the range of about 0.5 V to about 1.5 V.

28. The method of claim 1 wherein the magnitude of the voltage is in the range of about 0.6 V to about 1.2 V.

29. The method of claim 1 wherein the magnitude of the voltage is in the range of about 0.8 V to about 1.2 V.

30. The method of claim 1 wherein the voltage applied results in a current density in the range of about 5 µA/cm² to about 200 µA/cm² on at least the outer surface of the catheter body.

31. The method of claim 1 wherein the voltage applied results in a current density in the range of about 10 µA/cm² to about 200 µA/cm² on at least the outer surface of the catheter body.

32. The method of claim 1 wherein the voltage applied results in a current density in the range of about 20 µA/cm² to about 200 µA/cm² on at least the outer surface of the catheter body.

33. The method of claim 1 further comprising determining blood oxygen concentration at the outer surface.

34. The method of claim 1 further comprising measuring impedance across the exterior electrodes and communicating the measurement to an external device.

35. The method of claim 1 wherein the method further comprises confirming the presence or formation of a biofilm on at least the outer surface of the catheter prior to applying a voltage across the external electrodes.

36. The method of claim 1 wherein the method further comprises confirming the presence or formation of a biofilm on at least the outer surface of the catheter prior to applying a voltage across the external electrodes, wherein the confirming comprises detecting an increase in impedance across the external electrodes relative to the impedance across the electrodes in the absence of a biofilm.

37. The method of claim 1 wherein the method further comprises confirming the presence or formation of a biofilm on at least the outer surface of the catheter prior to applying a voltage across the external electrodes, wherein the confirming comprises detecting an increase in impedance across the external electrodes relative to the impedance across the electrodes in the absence of a biofilm, wherein the detecting of an increase in impedance comprises applying a voltage in the range of about 10 mV to about 30 mV across the external electrodes while measuring the impedance across the electrodes, and comparing the impedance measured with the impedance observed across the electrodes in the absence of a biofilm.

38. The method of claim 1 wherein the method further comprises confirming the presence or formation of a biofilm on at least the outer surface of the catheter prior to applying a voltage across the external electrodes, and then measuring the thickness of the biofilm present.

39. The method of claim 1 wherein the method further comprises confirming the presence or formation of a biofilm on at least the outer surface of the catheter prior to applying a voltage across the external electrodes, and then measuring the thickness of the biofilm present, and then adjusting the magnitude and duration of voltage applied to ensure that the biofilm is destroyed.

40. The method of claim 1 wherein the method further comprises confirming the presence or formation of a biofilm on at least the outer surface of the catheter prior to applying a voltage across the external electrodes, wherein the confirming comprises detecting a decrease in the amount of oxygen present in the region of the outer surface of the catheter.

41. The method of claim 1 wherein:
the catheter body is comprised of a flexible elastomeric material comprising silicone or polyurethane; and
the electrodes are comprised of a carbon-polymer composite.

42. The method of claim 1 wherein:
the catheter body is comprised of a flexible elastomeric material comprising silicone or polyurethane;
the electrodes are comprised of a carbon-polymer composite, and
each gap is in the range of about 1000 Å to about 2 µm.

43. The method of claim 1 wherein:
the catheter body is comprised of a flexible elastomeric material comprising silicone or polyurethane;
the electrodes are comprised of a carbon-polymer composite, and
each gap is in the range of about 10 µm to about 200 µm.

44. The method of claim 1 wherein the electrodes extend through the catheter body to a distal terminus of the catheter.

45. The method of claim 1 wherein:
the catheter body is comprised of a flexible elastomeric material comprising silicone or polyurethane;
the electrodes are comprised of a carbon-polymer composite; and
the electrodes extend through the catheter body to a distal terminus of the catheter.

46. The method of claim 1 wherein:
the catheter body is comprised of a flexible elastomeric material comprising silicone or polyurethane;
the electrodes are comprised of a carbon-polymer composite,
each gap is in the range of about 1000 Å to about 2 µm; and
the electrodes extend through the catheter body to a distal terminus of the catheter.

47. The method of claim 1 wherein:
the catheter body is comprised of a flexible elastomeric material comprising silicone or polyurethane;
the electrodes are comprised of a carbon-polymer composite;
each gap is in the range of about 10 µm to about 200 µm; and
the electrodes extend through the catheter body to a distal terminus of the catheter.

48. The method of claim 1 wherein:
the catheter body is comprised of a flexible elastomeric material comprising silicone or polyurethane;
the electrodes are comprised of a carbon-polymer composite;
each gap is in the range of about 10 µm to about 200 µm; and
the electrodes extend through the catheter body to a distal terminus of the catheter, wherein the method effectively inhibits the biofilm at the distal region of the catheter.

* * * * *